United States Patent
Li et al.

(10) Patent No.: US 10,556,947 B2
(45) Date of Patent: *Feb. 11, 2020

(54) BINDING MOLECULE THAT BINDS SPECIFICALLY TO THE PRECURSOR OF BRAIN-DERIVED NEUROTROPHIC FACTOR

(71) Applicant: SHANGHAI YILE BIOTECHNOLOGY CO., LTD., Shanghai (CN)

(72) Inventors: Changqi Li, Shanghai (CN); Huamao Wang, Shanghai (CN); Ruping Dai, Shanghai (CN); Xiumei Cai, Shanghai (CN); Xinfu Zhou, Shanghai (CN)

(73) Assignee: Shanghai Yile Biotechnology Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/627,305

(22) Filed: Jun. 19, 2017

(65) Prior Publication Data
US 2017/0362313 A1    Dec. 21, 2017

Related U.S. Application Data

(63) Continuation-in-part of application No. PCT/CN2015/097820, filed on Dec. 18, 2015.

(30) Foreign Application Priority Data

Dec. 19, 2014   (CN) .......................... 2014 1 0811678

(51) Int. Cl.
*C07K 16/22* (2006.01)
*A61K 39/00* (2006.01)

(52) U.S. Cl.
CPC ........ *C07K 16/22* (2013.01); *A61K 2039/505* (2013.01); *A61K 2039/545* (2013.01); *C07K 2317/51* (2013.01); *C07K 2317/515* (2013.01); *C07K 2317/56* (2013.01); *C07K 2317/565* (2013.01); *C07K 2317/76* (2013.01)

(58) Field of Classification Search
CPC ................. C07K 16/22; C07K 2317/24; C07K 2317/56; C07K 2317/565; C07K 2317/76; C07K 2317/92; A61K 2039/505
See application file for complete search history.

(56) References Cited

FOREIGN PATENT DOCUMENTS

| EP | 3095796 A1 | 11/2016 |
|---|---|---|
| WO | WO-2010093904 A2 | 8/2010 |
| WO | WO-2010093904 A3 | 1/2011 |
| WO | WO-2011035465 A1 | 3/2011 |
| WO | WO-2015106641 A1 | 7/2015 |
| WO | WO-2016095839 A1 | 6/2016 |

OTHER PUBLICATIONS

Martins TB et al. Analysis of proinflammatory and anti-inflammatory cytokine serum concentrations in patients with multiple sclerosis by using a multplexed immunoassay. Am. J. Clin. Pathol. 2011, 136:696-704. (Year: 2011).*
Moudgil KD & Choubey D. Cytokines in autoimmunity: Role in induction, regulation, and treatment. J. Interferon & Cytokine Res. 31 (10):695-703. (Year: 2011).*
Su DL et al. Roles of pro- and anti-inflammatory cytokines in the pathogenesis of SLE. J. Biomed. Biotech. vol. 2012, pp. 1-15. (Year: 2012).*
Wikipedia entry for "Interferon", retrieved from internet May 14, 2018, 11 pages. (Year: 2018).*
Lin YT et al. Up-regulation of dorsal root ganglia BDNF and trkB in inflammatory pain: an in vivo and in vitro study. J. Neuroinflammation, 2011, 8:126, 22 pages. (Year: 2011).*
Fregnan F et al. Role of inflammatory cytokines in peripheral nerve injury. Neural Regen. Res. Oct. 2012, 7(29):2259-2266.*
Fan YJ et al. Differential effects of pro-BDNF on sensory neurons after sciatic nerve transection in neonatal rats. Eur. J. Neuroscience, 27:2380-2390. (Year: 2008).*
Taskinen HS et al. Peripheral nerve injury induces endoneurial expression of IFN-gamma, IL-10 and TNF-alpha mRNA. J. Neuroimmunol. 2000, 102:17-25. (Year: 2000).*
Paul WE, Editor. Fundamental Immunology, Third Edition, 1993, Raven Press, New York, pp. 292-295. (Year: 1993).*
Rudikkoff S et al. Single amino acid substitution altering antigen-binding specificity. Proc Natl Acad Sci USA, 79:1979-1983. (Year: 1982).*
International Preliminary Report on Patentability dated Jun. 20, 2017 for PCT Application CN 2015097820.
International search report and written opinion dated Mar. 24, 2016 for PCT Application CN2015/097820.
Luo et al. Advancement in Research on Biological Effects of ProBDNF, Progress in Modern Biomedicine, 12(1):151-154 (2012).
De Santi, et al. Brain-derived neurotrophic factor and TrkB receptor in experimental autoimmune encephalomyelitis and multiple sclerosis. J Neurol Sci. Dec. 15, 2009;287(1-2):17-26. doi: 10.1016/j.jns.2009.08.057. Epub Sep. 16, 2009.
European search report with written opinion dated May 24, 2018 for EP Application No. 15869346.
Linker, et al. Functional role of brain-derived neurotrophic factor in neuroprotective autoimmunity: therapeutic implications in a model of multiple sclerosis. Brain. Aug. 2010;133(Pt 8):2248-63. doi: 10.1093/brain/awq179.

* cited by examiner

*Primary Examiner* — Kimberly Ballard
(74) *Attorney, Agent, or Firm* — Wilson Sonsini Goodrich & Rosati

(57) ABSTRACT

Disclosed herein is use of a binding molecule which specifically binds to a precursor of brain-derived neurotrophic factor (proBDNF). The binding molecule for proBDNF, especially a monoclonal antibody against proBDNF, can be used to prevent, mitigate or treat autoimmune diseases.

17 Claims, 11 Drawing Sheets
Specification includes a Sequence Listing.

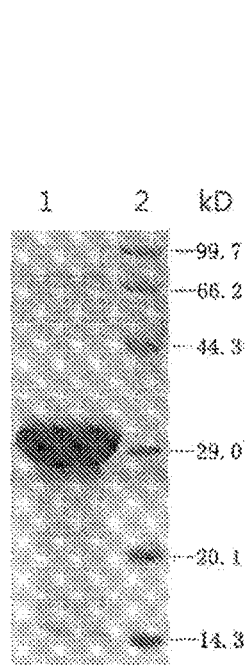
FIG. 1
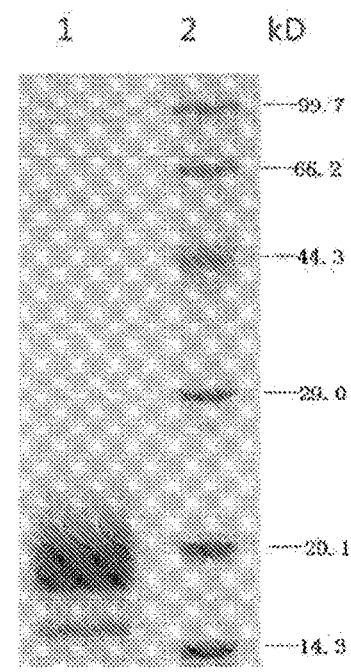
FIG. 2
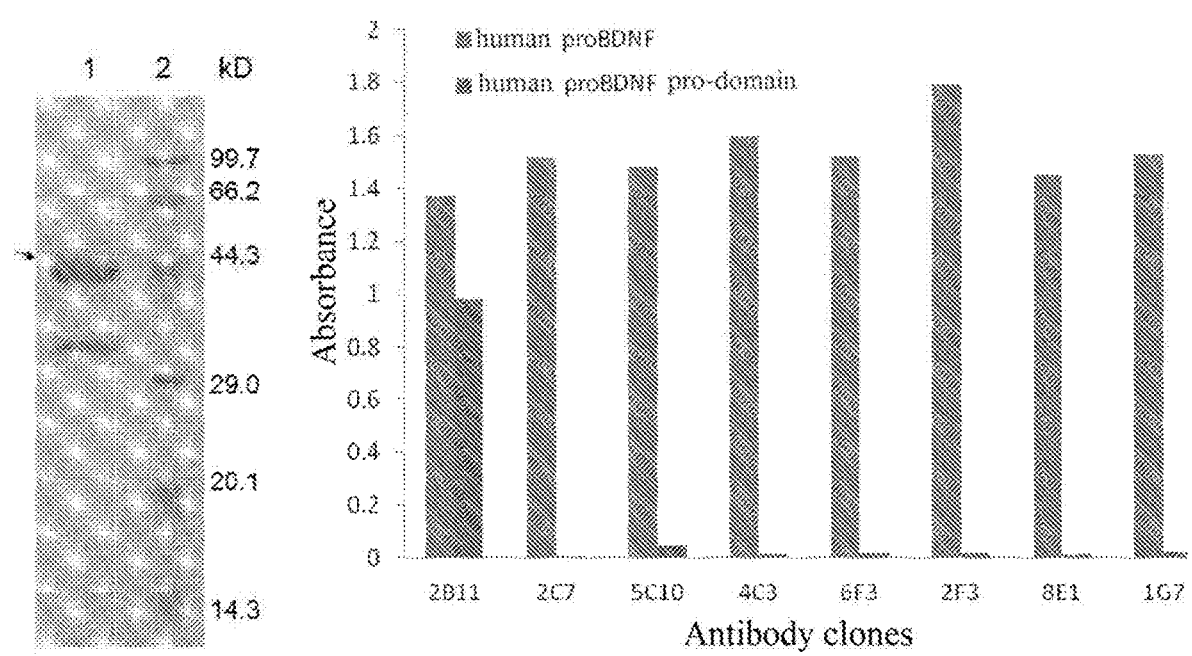
FIG. 3
FIG. 4

BINDING MOLECULE THAT BINDS SPECIFICALLY TO THE PRECURSOR OF BRAIN-DERIVED NEUROTROPHIC FACTOR

CROSS-REFERENCE TO RELATED APPLICATIONS

This application is a continuation-in-part of PCT Application No. PCT/CN2015/097820, filed Dec. 18, 2015, which claims the benefit of Chinese Patent Application No. 201410811678.8, filed on Dec. 19, 2014, both of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 5, 2017, is named 52380_701_501_SL.txt and is 20,606 bytes in size.

TECHNICAL FIELD

The present invention relates to the field of biopharmaceutics, and more particularly to use of a binding molecule which specifically binds to a precursor of brain-derived neurotrophic factor (proBDNF).

BACKGROUND OF THE INVENTION

Autoimmune diseases (AIDs) refer to a class of diseases in which autoimmune tolerance is disrupted, and the immune system is activated to attack self-antigens, leading to damage of tissues or organs. AIDs currently are considered as hypersensitivity diseases against self-antigens caused by autoantibodies, auto-reactive T lymphocytes or both. AIDs can be divided into two categories, i.e., organ-specific AIDs and systemic AIDs. The organ-specific autoimmune diseases refer to diseases in which the pathological damage and dysfunction of a tissue or organ are only limited to the organ to which the antibody or sensitized lymphocyte is directed, and examples of which mainly include Hashimoto's thyroiditis, toxic diffuse goiter, insulin-dependent diabetes mellitus, myasthenia gravis, autoimmune thrombocytopenic purpura, autoimmune hemolytic anemia, pernicious anemia, Goodpasture's syndrome, pemphigus vulgaris, etc. The systemic autoimmune diseases refer to damages to multiple organs in the whole body due to, for example, the wide deposition of an antigen-antibody complex in the blood vessel wall, including systemic lupus erythematosus, rheumatoid arthritis, ankylosing spondylitis, cryoglobulinemia, multiple sclerosis, etc.

There has been no cure for AIDs. Although traditional glucocorticoids and immunosuppressive agents can control the disease and improve the survival rate of patients when administered timely, long-term use thereof brings about a series of side effects, which can affect the life quality of patients, or even can be life-threatening in severe cases. Moreover, some patients may be insensitive to the treatments with glucocorticoids and immunosuppressive agents. In recent years, new therapeutic strategies have been proposed, including gene therapy, epigenetic intervention, a small molecule Toll-like receptor inhibitor, an anti-inflammatory factor antibody, B-cell depletion, autotransfusion of stem cells and regulatory T cells, a dendritic cell vaccine, etc. Some of these therapeutic drugs or methods have been used clinically (such as belimumab, rituximab, etc.), and some are still under clinical research (such as stem cell autotransfusion therapy, and the like), or even at the stage of animal testing (such as epigenetic regulation, and the like). However, these drugs cannot replace glucocorticoids as first-line drugs. Thus there exist a pressing need for alternative effective therapeutic drugs and methods for clinical application.

Brain-derived neurotrophic factor (BDNF) of a molecular weight of 12.4 kDa is a neurotrophic factor found after the discovery of the nerve growth factor. It is mainly distributed in the central nervous system, but is also in the peripheral nervous system. BDNF has important functions in the regulation of neuronal survival, differentiation, synaptic plasticity, damage repair, etc. Currently, there is evidence that BDNF is not only an important factor in the regulation of nervous system development and affective disorder, but also an important pain modulator.

The precursor of brain-derived neurotrophic factor (proBDNF) is synthesized in the endoplasmic reticulum through transcription and translation from the BDNF gene. The resulting peptide chain has 247 amino acids. Its amino acid sequence has a theoretical molecular weight of 27.8 kD, but the actual molecular weight can vary in the range of 32-36 kD due to different degrees of protein glycosylation modification. A signal peptide sequence is located at positions 1-18 of the amino acid sequence of proBDNF. Two fragments are produced during protein secretion: a polypeptide fragment (known as proBDNF pro-domain) comprising amino acids 19-129 of the sequence, i.e., a precursor domain; and a fragment encoded by amino acids 130-247 of the sequence, i.e., a mature domain, which fragment forms a mature BDNF with bioactivity after being processed.

Currently, there is considerable evidence that proBDNF not only acts as an intermediate for the synthesis of mature BDNF, but also can be used as a ligand that mediates biological effects in conjunction with its high affinity receptor p75 neurotrophin receptor (p75NTR). Researches show that precursors of neurotrophic factor (including proNGF, proBDNF, etc.) can promote apoptosis and inflammatory responses. However, the roles of proBDNF and its signaling in autoimmune diseases has not been reported.

SUMMARY OF THE INVENTION

An objective of the present invention is to provide methods of using a binding molecule which specifically binds to a precursor of brain-derived neurotrophic factor (proBDNF).

In the first aspect of the present invention, provided is a method for preventing, mitigating or treating an autoimmune disease, comprising administering to a subject in need thereof a binding molecule which specifically binds to a precursor of brain-derived neurotrophic factor. In a preferred embodiment, the binding molecule which specifically binds to a precursor of brain-derived neurotrophic factor is a monoclonal antibody comprising a heavy chain variable region having a CDR1 region as shown in SEQ ID NO: 1, a CDR2 region as shown in SEQ ID NO: 2 and a CDR3 region as shown in SEQ ID NO: 3; and a light chain variable region having a CDR1 region as shown in SEQ ID NO: 4, a CDR2 region as shown in SEQ ID NO: 5 and a CDR3 region as shown in SEQ ID NO: 6. In another preferred embodiment, the binding molecule which specifically binds to a precursor of brain-derived neurotrophic factor is a monoclonal antibody, which specifically recognizes the polypeptide comprising the amino acid sequence from amino acid 19 to 128 in the proBDNF protein pro-domain. In another preferred embodiment, the heavy chain variable region of the monoclonal antibody has an amino acid sequence as shown in SEQ ID NO: 7; and the light chain variable region of the monoclonal antibody has an amino acid sequence as shown in SEQ ID NO: 8. In another preferred embodiment, the heavy chain variable region of the monoclonal antibody has a nucleotide sequence as shown in SEQ ID NO: 11; or the light chain variable region of the monoclonal antibody has a nucleotide sequence as shown in SEQ ID NO: 12. In another preferred embodiment, the heavy chain of the monoclonal antibody has an amino acid sequence as shown in SEQ ID NO: 9; or the light chain of the monoclonal antibody has an amino acid sequence as shown in SEQ ID NO: 10. In another preferred embodiment, the heavy chain of the monoclonal antibody has a nucleotide sequence as shown in SEQ ID NO: 13; or the light chain of the monoclonal antibody has a nucleotide sequence as shown in SEQ ID NO: 14. In another preferred embodiment, the binding molecule which specifically binds to a precursor of brain-derived neurotrophic factor is a polyclonal antibody. In another preferred embodiment, the polyclonal antibody is produced by immunizing an animal with a precursor of brain-derived neurotrophic factor, or a protein fragment thereof, preferably, a fragment comprising an amino acid sequence as shown in SEQ ID NO: 37. In another preferred embodiment, the binding molecule which specifically binds to a precursor of brain-derived neurotrophic factor is an antibody, including, but not limited to, a fully human antibody, a humanized antibody, a chimeric antibody, an affinity-matured antibody, a murine-derived antibody, or a combination thereof. In another preferred embodiment, the binding precursor of brain-derived neurotrophic factor is a human binding precursor of brain-derived neurotrophic factor. In another preferred embodiment, the autoimmune disease is a systemic autoimmune disease. In another preferred embodiment, the autoimmune disease includes, but is not limited to, rheumatoid arthritis, ankylosing spondylitis, psoriasis, systemic lupus erythematosus, insulin-dependent diabetes mellitus (such as Type I Diabetes Mellitus), multiple sclerosis, aplastic anemia, cryoglobulinemia, or a combination thereof. In another preferred embodiment, the binding molecule is administered by intravenous or intraperitoneal injection. In another preferred embodiment, the binding molecule also mitigates neurologic impairment; inhibits inflammatory cytokine infiltration in the central nervous system; alleviates myelin sheath loss in the spinal white matter; or reduces the expression of IL-1, IL-6, IL-17, IFN-γ or TNF-α. In another embodiment, the binding molecule is administered to the subject at an amount in the range of 0.1-100 mg/kg body weight, or 0.5-15 mg/kg body weight.

In another aspect of the present invention, provided is a method for inhibiting an interleukin (IL) production, comprising administering to a subject in need thereof a binding molecule which specifically binds to a precursor of brain-derived neurotrophic factor. In an embodiment of the present invention, the interleukin is selected from one or more of IL-1, IL6, and IL-17. In a preferred embodiment, the binding molecule which specifically binds to a precursor of brain-derived neurotrophic factor is a monoclonal antibody comprising a heavy chain variable region having a CDR1 region as shown in SEQ ID NO: 1, a CDR2 region as shown in SEQ ID NO: 2 and a CDR3 region as shown in SEQ ID NO: 3; and a light chain variable region having a CDR1 region as shown in SEQ ID NO: 4, a CDR2 region as shown in SEQ ID NO: 5 and a CDR3 region as shown in SEQ ID NO: 6. In another preferred embodiment, the binding molecule which specifically binds to a precursor of brain-derived neurotrophic factor is a monoclonal antibody, which specifically recognizes the polypeptide comprising the amino acid sequence from amino acid 19 to 128 in the proBDNF protein pro-domain. In another preferred embodiment, the heavy chain variable region of the monoclonal antibody has an amino acid sequence as shown in SEQ ID NO: 7; and the light chain variable region of the monoclonal antibody has an amino acid sequence as shown in SEQ ID NO: 8. In another preferred embodiment, the heavy chain variable region of the monoclonal antibody has a nucleotide sequence as shown in SEQ ID NO: 11; or the light chain variable region of the monoclonal antibody has a nucleotide sequence as shown in SEQ ID NO: 12. In another preferred embodiment, the heavy chain of the monoclonal antibody has an amino acid sequence as shown in SEQ ID NO: 9; or the light chain of the monoclonal antibody has an amino acid sequence as shown in SEQ ID NO: 10. In another preferred embodiment, the heavy chain of the monoclonal antibody has a nucleotide sequence as shown in SEQ ID NO: 13; or the light chain of the monoclonal antibody has a nucleotide sequence as shown in SEQ ID NO: 14. In another preferred embodiment, the binding molecule which specifically binds to a precursor of brain-derived neurotrophic factor is a polyclonal antibody. In another preferred embodiment, the polyclonal antibody is produced by immunizing an animal with a precursor of brain-derived neurotrophic factor, or a protein fragment thereof, preferably, a fragment comprising an amino acid sequence as shown in SEQ ID NO: 37. In another preferred embodiment, the binding molecule which specifically binds to a precursor of brain-derived neurotrophic factor is an antibody, including, but not limited to, a fully human antibody, a humanized antibody, a chimeric antibody, an affinity-matured antibody, a murine-derived antibody, or a combination thereof. In another preferred embodiment, the binding precursor of brain-derived neurotrophic factor is a human binding precursor of brain-derived neurotrophic factor. In another embodiment, the binding molecule is administered to the subject at an amount in the range of 0.1-100 mg/kg body weight, or 0.5-15 mg/kg body weight.

In another aspect of the present invention, provided is a method for inhibiting an interferon (IFN) production, comprising administering to a subject in need thereof a binding molecule which specifically binds to a precursor of brain-derived neurotrophic factor. In an embodiment of the present invention, the interferon comprises IFN-γ. In a preferred embodiment, the binding molecule which specifically binds to a precursor of brain-derived neurotrophic factor is a monoclonal antibody comprising a heavy chain variable region having a CDR1 region as shown in SEQ ID NO: 1, a CDR2 region as shown in SEQ ID NO: 2 and a CDR3 region as shown in SEQ ID NO: 3; and a light chain variable region having a CDR1 region as shown in SEQ ID NO: 4, a CDR2 region as shown in SEQ ID NO: 5 and a CDR3 region as shown in SEQ ID NO: 6. In another preferred embodiment, the binding molecule which specifically binds to a precursor of brain-derived neurotrophic factor is a monoclonal antibody, which specifically recognizes the polypeptide comprising the amino acid sequence from amino acid 19 to 128 in the proBDNF protein pro-domain. In another preferred embodiment, the heavy chain variable region of the monoclonal antibody has an amino acid sequence as shown in SEQ ID NO: 7; and the light chain variable region of the monoclonal antibody has an amino acid sequence as shown in SEQ ID NO: 8. In another preferred embodiment, the heavy chain variable region of the monoclonal antibody has a nucleotide sequence as shown in SEQ ID NO: 11; or the light chain variable region of the monoclonal antibody has a nucleotide sequence as shown in SEQ ID NO: 12. In another preferred embodiment, the heavy chain of the monoclonal antibody has an amino acid sequence as shown in SEQ ID NO: 9; or the light chain of the monoclonal antibody has an amino acid sequence as shown in SEQ ID NO: 10. In another preferred embodiment, the heavy chain of the monoclonal antibody has a nucleotide sequence as shown in SEQ ID NO: 13; or the light chain of the monoclonal antibody has a nucleotide sequence as shown in SEQ ID NO: 14. In another preferred embodiment, the binding molecule which specifically binds to a precursor of brain-derived neurotrophic factor is a polyclonal antibody. In another preferred embodiment, the polyclonal antibody is produced by immunizing an animal with a precursor of brain-derived neurotrophic factor, or a protein fragment thereof, preferably, a fragment comprising an amino acid sequence as shown in SEQ ID NO: 37. In another preferred embodiment, the binding molecule which specifically binds to a precursor of brain-derived neurotrophic factor is an antibody, including, but not limited to, a fully human antibody, a humanized antibody, a chimeric antibody, an affinity-matured antibody, a murine-derived antibody, or a combination thereof. In another preferred embodiment, the binding precursor of brain-derived neurotrophic factor is a human binding precursor of brain-derived neurotrophic factor. In another embodiment, the binding molecule is administered to the subject at an amount in the range of 0.1-100 mg/kg body weight, or 0.5-15 mg/kg body weight.

In another aspect of the present invention, provided is a method for inhibiting a tumor necrosis factor production, comprising administering to a subject in need thereof a binding molecule which specifically binds to a precursor of brain-derived neurotrophic factor. In an embodiment of the present invention, the tumor necrosis factor comprises TNF-α. In a preferred embodiment, the binding molecule which specifically binds to a precursor of brain-derived neurotrophic factor is a monoclonal antibody comprising a heavy chain variable region having a CDR1 region as shown in SEQ ID NO: 1, a CDR2 region as shown in SEQ ID NO: 2 and a CDR3 region as shown in SEQ ID NO: 3; and a light chain variable region having a CDR1 region as shown in SEQ ID NO: 4, a CDR2 region as shown in SEQ ID NO: 5 and a CDR3 region as shown in SEQ ID NO: 6. In another preferred embodiment, the binding molecule which specifically binds to a precursor of brain-derived neurotrophic factor is a monoclonal antibody, which specifically recognizes the polypeptide comprising the amino acid sequence from amino acid 19 to 128 in the proBDNF protein pro-domain. In another preferred embodiment, the heavy chain variable region of the monoclonal antibody has an amino acid sequence as shown in SEQ ID NO: 7; and the light chain variable region of the monoclonal antibody has an amino acid sequence as shown in SEQ ID NO: 8. In another preferred embodiment, the heavy chain variable region of the monoclonal antibody has a nucleotide sequence as shown in SEQ ID NO: 11; or the light chain variable region of the monoclonal antibody has a nucleotide sequence as shown in SEQ ID NO: 12. In another preferred embodiment, the heavy chain of the monoclonal antibody has an amino acid sequence as shown in SEQ ID NO: 9; or the light chain of the monoclonal antibody has an amino acid sequence as shown in SEQ ID NO: 10. In another preferred embodiment, the heavy chain of the monoclonal antibody has a nucleotide sequence as shown in SEQ ID NO: 13; or the light chain of the monoclonal antibody has a nucleotide sequence as shown in SEQ ID NO: 14. In another preferred embodiment, the binding molecule which specifically binds to a precursor of brain-derived neurotrophic factor is a polyclonal antibody. In another preferred embodiment, the polyclonal antibody is produced by immunizing an animal with a precursor of brain-derived neurotrophic factor, or a protein fragment thereof, preferably, a fragment comprising an amino acid sequence as shown in SEQ ID NO: 37. In another preferred embodiment, the binding molecule which specifically binds to a precursor of brain-derived neurotrophic factor is an antibody, including, but not limited to, a fully human antibody, a humanized antibody, a chimeric antibody, an affinity-matured antibody, a murine-derived antibody, or a combination thereof. In another preferred embodiment, the binding precursor of brain-derived neurotrophic factor is a human binding precursor of brain-derived neurotrophic factor. In another embodiment, the binding molecule is administered to the subject at an amount in the range of 0.1-100 mg/kg body weight, or 0.5-15 mg/kg body weight.

In another aspect of the present invention, provided is a pharmaceutical composition for treating an autoimmune disease, comprising at least one binding molecule which specifically binds to a precursor of brain-derived neurotrophic factor and a pharmaceutically acceptable carrier, wherein the binding molecule is in an amount effective in treating autoimmune diseases. In a preferred embodiment, the binding molecule which specifically binds to a precursor of brain-derived neurotrophic factor is a monoclonal antibody comprising a heavy chain variable region having a CDR1 region as shown in SEQ ID NO: 1, a CDR2 region as shown in SEQ ID NO: 2 and a CDR3 region as shown in SEQ ID NO: 3; and a light chain variable region having a CDR1 region as shown in SEQ ID NO: 4, a CDR2 region as shown in SEQ ID NO: 5 and a CDR3 region as shown in SEQ ID NO: 6. In another preferred embodiment, the binding molecule which specifically binds to a precursor of brain-derived neurotrophic factor is a monoclonal antibody, which specifically recognizes the polypeptide comprising the amino acid sequence from amino acid 19 to 128 in the proBDNF protein pro-domain. In another preferred embodiment, the heavy chain variable region of the monoclonal antibody has an amino acid sequence as shown in SEQ ID NO: 7; and the light chain variable region of the monoclonal antibody has an amino acid sequence as shown in SEQ ID NO: 8. In another preferred embodiment, the heavy chain variable region of the monoclonal antibody has a nucleotide sequence as shown in SEQ ID NO: 11; or the light chain variable region of the monoclonal antibody has a nucleotide sequence as shown in SEQ ID NO: 12. In another preferred embodiment, the heavy chain of the monoclonal antibody has an amino acid sequence as shown in SEQ ID NO: 9; or the light chain of the monoclonal antibody has an amino acid sequence as shown in SEQ ID NO: 10. In another preferred embodiment, the heavy chain of the monoclonal antibody has a nucleotide sequence as shown in SEQ ID NO: 13; or the light chain of the monoclonal antibody has a nucleotide sequence as shown in SEQ ID NO: 14. In another preferred embodiment, the binding molecule which specifically binds to a precursor of brain-derived neurotrophic factor is a polyclonal antibody. In another preferred embodiment, the polyclonal antibody is produced by immunizing an animal with a precursor of brain-derived neurotrophic factor, or a protein fragment thereof, preferably, a fragment comprising an amino acid sequence as shown in SEQ ID NO: 37. In another preferred embodiment, the binding molecule which specifically binds to a precursor of brain-derived neurotrophic factor is an antibody, including, but not limited to, a fully human antibody, a humanized antibody, a chimeric antibody, an affinity-matured antibody, a murine-derived antibody, or a combination thereof. In another preferred embodiment, the binding precursor of brain-derived neurotrophic factor is a human binding precursor of brain-derived neurotrophic factor. In another preferred embodiment, the autoimmune disease is a systemic autoimmune disease. In another preferred embodiment, the autoimmune disease includes, but is not limited to, rheumatoid arthritis, ankylosing spondylitis, psoriasis, systemic lupus erythematosus, insulin-dependent diabetes mellitus (such as Type I Diabetes Mellitus), multiple sclerosis, aplastic anemia, cryoglobulinemia, or a combination thereof. In another preferred embodiment, the binding molecule is administered by intravenous or intraperitoneal injection. In another preferred embodiment, the binding molecule also mitigates neurologic impairment; inhibits inflammatory cytokine infiltration in the central nervous system; alleviates myelin sheath loss in the spinal white matter; or reduces the expression of IL-1, IL-6, IL-17, IFN-γ or TNF-α. In another embodiment, the binding molecule is administered to the subject at an amount in the range of 0.1-100 mg/kg body weight, or 0.5-15 mg/kg body weight. In another embodiment, the composition further comprises another therapeutic agent for autoimmune diseases.

In another aspect of the present invention, provided is a kit comprising at least one binding molecule which specifically binds to a precursor of brain-derived neurotrophic factor and an instruction for treating a subject suffering from an autoimmune disease with the kit. In a preferred embodiment, the binding molecule which specifically binds to a precursor of brain-derived neurotrophic factor is a monoclonal antibody comprising a heavy chain variable region having a CDR1 region as shown in SEQ ID NO: 1, a CDR2 region as shown in SEQ ID NO: 2 and a CDR3 region as shown in SEQ ID NO: 3; and a light chain variable region having a CDR1 region as shown in SEQ ID NO: 4, a CDR2 region as shown in SEQ ID NO: 5 and a CDR3 region as shown in SEQ ID NO: 6. In another preferred embodiment, the binding molecule which specifically binds to a precursor of brain-derived neurotrophic factor is a monoclonal antibody, which specifically recognizes the polypeptide comprising the amino acid sequence from amino acid 19 to 128 in the proBDNF protein pro-domain. In another preferred embodiment, the heavy chain variable region of the monoclonal antibody has an amino acid sequence as shown in SEQ ID NO: 7; and the light chain variable region of the monoclonal antibody has an amino acid sequence as shown in SEQ ID NO: 8. In another preferred embodiment, the heavy chain variable region of the monoclonal antibody has a nucleotide sequence as shown in SEQ ID NO: 11; or the light chain variable region of the monoclonal antibody has a nucleotide sequence as shown in SEQ ID NO: 12. In another preferred embodiment, the heavy chain of the monoclonal antibody has an amino acid sequence as shown in SEQ ID NO: 9; or the light chain of the monoclonal antibody has an amino acid sequence as shown in SEQ ID NO: 10. In another preferred embodiment, the heavy chain of the monoclonal antibody has a nucleotide sequence as shown in SEQ ID NO: 13; or the light chain of the monoclonal antibody has a nucleotide sequence as shown in SEQ ID NO: 14. In another preferred embodiment, the binding molecule which specifically binds to a precursor of brain-derived neurotrophic factor is a polyclonal antibody. In another preferred embodiment, the polyclonal antibody is produced by immunizing an animal with a precursor of brain-derived neurotrophic factor, or a protein fragment thereof, preferably, a fragment comprising an amino acid sequence as shown in SEQ ID NO: 37. In another preferred embodiment, the binding molecule which specifically binds to a precursor of brain-derived neurotrophic factor is an antibody, including, but not limited to, a fully human antibody, a humanized antibody, a chimeric antibody, an affinity-matured antibody, a murine-derived antibody, or a combination thereof. In another preferred embodiment, the binding precursor of brain-derived neurotrophic factor is a human binding precursor of brain-derived neurotrophic factor. In another preferred embodiment, the autoimmune disease is a systemic autoimmune disease. In another preferred embodiment, the autoimmune disease includes, but is not limited to, rheumatoid arthritis, ankylosing spondylitis, psoriasis, systemic lupus erythematosus, insulin-dependent diabetes mellitus (such as Type I Diabetes Mellitus), multiple sclerosis, aplastic anemia, cryoglobulinemia, or a combination thereof. In another preferred embodiment, the binding molecule is administered by intravenous or intraperitoneal injection. In another preferred embodiment, the binding molecule also mitigates neurologic impairment; inhibits inflammatory cytokine infiltration in the central nervous system; alleviates myelin sheath loss in the spinal white matter; or reduces the expression of IL-1, IL-6, IL-17, IFN-γ or TNF-α. In another embodiment, the binding molecule is administered to the subject at an amount in the range of 0.1-100 mg/kg body weight, or 0.5-15 mg/kg body weight. In another embodiment, the composition further comprises another therapeutic agent for autoimmune diseases.

Other aspects of the present invention will be apparent to those skilled in the art from the disclosure herein.

BRIEF DESCRIPTION OF THE DRAWINGS

FIG. 1 shows the results of SDS-PAGE electrophoresis of the purified human proBDNF protein expressed by a host strain BL21 (DE3) in Example 1. Lane 1: purified human proBDNF protein; Lane 2: Protein Molecular Weight Marker (Low), purchased from TAKARA, Cat. No. 3450.

FIG. 2 shows the results of SDA-PAGE electrophoresis of the purified human proBDNF pro-domain protein expressed by an HEK293F cell in Example 2 of the present invention. Lane 1: purified human pro-domain protein; Lane 2: Protein Molecular Weight Marker (Low), purchased from TAKARA, Cat. No. 3450.

FIG. 3 shows the results of SDS-PAGE electrophoresis of a rat proBDNF pro-domain fusion protein (rat proBDNF pro-domain-Fc). The molecular weight of the target band of lane 1 is about 44.3 kD (indicated by the arrow).

FIG. 4 shows binding of the specific antigen-binding regions of the anti-proBDNF monoclonal antibodies produced by individual hybridoma cell strains in Example 3 of the present invention to human proBDNF and human proBDNF pro-domain.

DETAILED DESCRIPTION OF THE INVENTION

Figure 5:
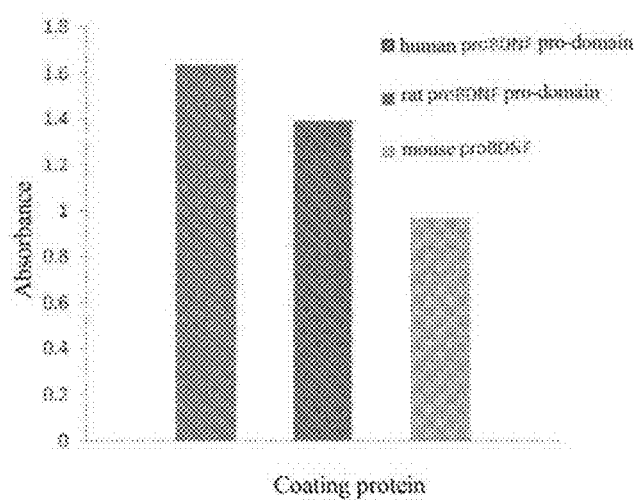
FIG. 5 shows binding of the specific antigen-binding regions of the anti-proBDNF monoclonal antibodies produced by individual hybridoma cell strains in Example 3 of the present invention to human proBDNF and mouse proBDNF.

The present disclosure is based, in part, on the discovery that the precursor of brain-derived neurotrophic factor (proBDNF) is an important target for the treatment of autoimmune diseases, and that the binding molecules which specifically bind to proBDNF (including anti-proBDNF monoclonal antibodies and polyclonal antibodies) have a significant alleviative or therapeutic effect on autoimmune diseases.

The present invention provides a binding molecule which can specifically bind to proBDNF, wherein the binding molecule exhibits a neutralizing or inhibitory activity against proBDNF.

The binding molecule of the present invention can be an intact immunoglobulin molecule such as a polyclonal or monoclonal antibody. Alternatively, the binding molecule can be an antigen-binding fragment, including, but not limited to, Fab, F(ab'), F(ab')$_2$, Fv, dAb, Fd, a complementarity determining region (CDR) fragment, a single chain antibody (scFv), a divalent single chain antibody, a single chain phage antibody, a bispecific double chain antibody, a triabody, a tetrabody, and a (poly)peptide containing at least an immunoglobulin fragment that is sufficient to specifically bind to proBDNF, or a fragment thereof. In a preferred embodiment, the binding molecule of the present invention is a human monoclonal antibody or polyclonal antibody.

As described in Kabat, et al. (1991), a CDR region is a protein sequence of immunological interest. In an embodiment of the present invention, the binding molecule can comprise two, three, four, five or all six CDR regions disclosed herein. Preferably, the binding molecule of the present invention comprises at least two CDRs disclosed herein.

Another aspect of the present invention comprises a functional variant of the binding molecule described herein. When a variant is capable of competing with a parental binding molecule for specifically binding to proBDNF or a protein fragment thereof, the variant molecule is considered to be a functional variant of the binding molecule of the present invention. For example, the functional variant still can bind to proBDNF or a fragment thereof. The functional variant includes, but is not limited to, derivatives that are substantially similar in primary structures and sequences, but contain, for example, in vitro or in vivo chemical and/or biochemical modifications which are not found in a parental binding molecule. Such modifications include acetylation, acylation, covalent attachment of a nucleotide or a derivative thereof, covalent attachment of a lipid or a derivative thereof, cross-linking, disulfide bond formation, glycosylation, hydroxylation, methylation, oxidation, pegylation, proteolytic processing, phosphorylation, and the like. In other words, the modifications in the amino acid and/or nucleotide sequence of the parental binding molecule do not significantly affect or alter the binding property of the binding molecule which is encoded by the nucleotide sequence or comprises the amino acid sequence, i.e., the binding molecule is still capable of recognizing and binding to its target site.

The functional variant can have a conservative sequence modification, including substitution, addition and deletion of a nucleotide and amino acid. These modifications can be introduced by the standard technology known in the art, such as directed mutagenesis and random PCR-mediated mutagenesis, and can comprise both natural and non-natural nucleotides and amino acids.

Conservative amino acid substitutions include substitutions in which an amino acid residue is replaced by another amino acid residue having a similar structure or chemical property. The families of amino acid residues having similar side chains have been defined in the art. These families include amino acids with basic side chains (e.g., lysine, arginine, and histidine), amino acids with acidic side chains (e.g., aspartic acid, and glutamic acid), amino acids with uncharged polar side chains (e.g., asparagine, glutamine, serine, threonine, tyrosine, cysteine, and tryptophan), amino acids with nonpolar side chains (e.g., glycine, alanine, valine, leucine, isoleucine, proline, phenylalanine, and methionine), amino acids with branched side chains (e.g., threonine, valine, and isoleucine), and amino acids with aromatic side chains (e.g., tyrosine, phenylalanine, and tryptophan). Those skilled in the art will appreciate that other classification methods for amino acid residue families can be used in addition to those described above. In addition, the variant can have a non-conservative amino acid substitution, for example, an amino acid is replaced by another amino acid residue having a different structure or chemical property. Similar small variation can also include amino acid deletion and/or insertion. A computer program well known in the art can be used to determine which amino acid residues can be substituted, inserted, or deleted without eliminating the immunological activity.

In addition, the functional variant can comprise a truncation at either or both of the amino terminal or the carboxyl terminal of an amino acid sequence. The functional variant of the present invention can have the same or different, higher or lower binding affinity as compared to the parental binding molecule, but still can bind to proBDNF or a fragment thereof. For example, the functional variant of the present invention can have an increased or decreased binding affinity for proBDNF or a fragment thereof as compared to the parental binding molecule. The functional variant within the scope of the present invention has an amino acid sequence homology of at least about 50% to about 99%, preferably at least about 60% to about 99%, more preferably at least about 70% to about 99%, even more preferably at least about 80% to about 99%, most preferably at least about 90% to about 99%, particularly at least about 95% to about 99%, and particularly at least about 97% to about 99% to the parental binding molecule described herein. The computer algorithms known to those skilled in the art, such as Gap or Bestfit, can be used to optimally align amino acid sequences for comparison and determine the same or similar amino acid residues. The functional variant can be obtained by altering the parental binding molecule or a portion thereof using a conventional molecular biological method known in the art, including, but not limited to, error-prone PCR, oligonucleotide-guided mutagenesis, site-directed mutagenesis, and heavy chain and/or light chain shuffling. In an embodiment, the functional variant of the present invention has a neutralizing activity against proBDNF. The neutralizing activity can be the same as or higher or lower than that of the parental binding molecule. The term "(human) binding molecule" as used herein also encompasses the functional variants of the (human) binding molecule.

In a preferred embodiment of the present invention, the binding molecule is a monoclonal antibody. The present invention provides a monoclonal antibody comprising a corresponding amino acid sequence of the monoclonal antibody, and a monoclonal antibody comprising a variable region chain of the monoclonal antibody. The present invention also provides any antibody comprising a light chain and a heavy chain containing the complementarity determining regions (CDRs), and any antibody in which the CDR regions have more than 90% (preferably more than 95%) homology to the CDRs of the monoclonal antibody of the present invention.

The antigen binding property of a monoclonal antibody can be described with respect to three specific regions located in heavy and light chain variable regions, referred to as complementarity determining regions (CDRs). The CDRs separate the variable region into four framework regions (FRs), and the amino acid sequences of the four FRs are relatively conservative and not directly involved in a binding reaction. These CDRs form a cyclic structure in which the β-sheets formed by the FRs are close to each other in the spatial structure, and the CDRs on the heavy chain and the CDRs on the corresponding light chain constitute an antigen-binding site of the antibody. The comparison of amino acid sequences of antibodies of the same type can be used to determine which amino acids constitute the FR or CDR regions.

The monoclonal antibody or antibody fragment used in the present invention can be a fully human, humanized, chimeric or murine-derived monoclonal antibody or antibody fragment. As used herein, the term "humanized antibody" refers to an antibody having an amino acid sequence corresponding to an antibody produced by a human, and/or an antibody prepared by a technique for preparing a humanized antibody known in the art and disclosed in the present application. The humanized antibody mainly refers to a re-expressed antibody which is engineered from a murine-derived (or other non-human) monoclonal antibody by gene cloning and DNA recombination techniques, in which most of the amino acid sequences are substituted by human sequences, and the affinity and specificity of the parental murine monoclonal antibody are substantially retained, while the heterology is reduced, thereby facilitating the application in human bodies. The humanized antibody includes a chimeric antibody, a reshaped antibody (also known as CDR grafting antibody), a resurfaced antibody or a fully-humanized antibody. The humanized antibody can also be produced by various methods known in the art; for example, the humanized antibody can be selected from a phage library which expresses human antibodies. The humanized antibody can also be prepared by introducing a human immunoglobulin site into a transgenic animal, such as a mouse with an endogenous immunoglobulin gene inactivated partially or completely. In addition, the humanized antibody can also be prepared by immortalizing a human B lymphocyte that produces an antibody against a particular antigen.

In a preferred embodiment of the present invention, there is provided an anti-proBDNF monoclonal antibody, which is capable of specifically recognizing amino acids 19 to 128 of the pro-domain of proBDNF, and comprises a heavy chain variable region comprising the following amino acid sequences: (a) a CDR1 region as shown in SEQ ID NO: 1, (b) a CDR2 region as shown in SEQ ID NO: 2, and (c) a CDR3 region as shown in SEQ ID NO: 3; and/or a light chain variable region comprising the following amino acid sequences: (d) a CDR1 region as shown in SEQ ID NO: 4, (e) a CDR2 region as shown in SEQ ID NO: 5, and (f) a CDR3 region as shown in SEQ ID NO: 6.

In some embodiments, the binding molecule of the present invention comprises a heavy chain variable region comprising the following amino acid sequences: (a) a CDR1 region exhibiting at least 50%, 55%, 60%, 65%, 70%, 75%, 80%, 85%, 90%, 91%, 92%, 93%, 94%, 95%, 96%, 97%, 98%, 99%, or up to about 100% sequence homology to SEQ ID NO: 1, (b) a CDR2 region exhibiting at least 50%, 55%, 60%, 65%, 70%, 75%, 80%, 85%, 90%, 91%, 92%, 93%, 94%, 95%, 96%, 97%, 98%, 99%, or up to about 100% sequence homology to SEQ ID NO: 2, and (c) a CDR3 region exhibiting at least 50%, 55%, 60%, 65%, 70%, 75%, 80%, 85%, 90%, 91%, 92%, 93%, 94%, 95%, 96%, 97%, 98%, 99%, or up to about 100% sequence homology to SEQ ID NO: 3; and/or a light chain variable region comprising the following amino acid sequences: (d) a CDR1 region exhibiting at least 50%, 55%, 60%, 65%, 70%, 75%, 80%, 85%, 90%, 91%, 92%, 93%, 94%, 95%, 96%, 97%, 98%, 99%, or up to about 100% sequence homology to SEQ ID NO: 4, (e) a CDR2 region exhibiting at least 50%, 55%, 60%, 65%, 70%, 75%, 80%, 85%, 90%, 91%, 92%, 93%, 94%, 95%, 96%, 97%, 98%, 99%, or up to about 100% sequence homology to SEQ ID NO: 5, and (f) a CDR3 region exhibiting at least 50%, 55%, 60%, 65%, 70%, 75%, 80%, 85%, 90%, 91%, 92%, 93%, 94%, 95%, 96%, 97%, 98%, 99%, or up to about 100% sequence homology to SEQ ID NO: 6.

The present invention further provides a nucleic acid molecule encoding at least one binding molecule and its functional variant of the present invention. Such a nucleic acid molecule can be used as an intermediate for cloning, for example, for use in the affinity maturation method as described above. In a preferred embodiment, the nucleic acid molecule is isolated or purified. The sequence of the DNA molecule can be obtained by a conventional technique or a hybridoma technique. The functional variants of these nucleic acid molecules also constitute part of the present invention. The functional variant is a nucleic acid sequence that can be translated directly by using standard genetic codes to provide the same amino acid sequence as the sequence translated from the parental nucleic acid molecule. Once the relevant sequence is obtained, it can be obtained in batch by a recombination method. The relevant sequence is usually obtained after being cloned into a vector, transfected into a cell, and then isolated from the proliferated host cell by a conventional method. In addition, the relevant sequence can also be synthesized by an artificial synthesis method.

The present invention further provides a vector comprising the appropriate DNA sequence as described above and an appropriate promoter or control sequence. The vector can be used to transform a suitable host cell to enable it to express a protein. The vector can be a eukaryotic vector or a prokaryotic vector.

The present invention further provides a host cell comprising the vector for expressing the desired multifunctional antibody polypeptide. A "host cell" comprises a single cell or cell culture, which can accept and has accepted a vector comprising the inserted polynucleotide. The host cell of the present invention can be any prokaryotic host cell or eukaryotic host cell, which is compatible with the vector used. Eukaryotic host cells, including yeast cells, insect cells, plant cells, mammalian cells, etc., can be preferred, because eukaryotic cells comprise complex post-translational modification (e.g., glycosylation) of the target protein, and thus are increasingly used in large-scale cultivations. The commonly used host cell lines include the monkey kidney cell line (COS-7 ATCC CRL 1651), the human embryonic kidney cell line 293 and a subcloned cell line thereof, the baby hamster kidney cell line (BHK, ATCC CCL10), the Chinese hamster ovary cell line (CHO), etc. Preferably, the eukaryotic host cell of the present invention is the CHO cell.

The binding molecule that specifically binds to proBDNF according to the present invention can also be a polyclonal antibody that specifically binds to proBDNF. As used in the present invention, the term "polyclonal antibody" refers to a group of globulins capable of specifically binding to an antigen, which are synthesized and secreted by plasma cells of a body after an immunological reaction is elicited in the body upon antigen challenge. The antigen is usually composed of a plurality of antigenic determinants. When one of the antigenic determinants stimulates the body, one B lymphocyte accepts this antigen, and produces an antibody that is called a monoclonal antibody. When the plurality of antigenic determinants stimulates the body, a variety of monoclonal antibodies are produced accordingly, and these mixed monoclonal antibodies constitute a polyclonal antibody. The polyclonal antibody offers advantages such as high titer, high specificity, strong affinity, good sensitivity, convenient human handling and quality control. In addition, the polyclonal antibody can be prepared relatively easily and more economically.

The polyclonal antibody can be prepared by various methods well known in the art. The proBDNF or a fragment thereof can be administered to an animal (e.g., sheep, rabbit, mouse, rat, etc.) to induce the production of a polyclonal antibody. Similarly, a cell expressing proBDNF or a fragment thereof can also be used to immunize an animal to produce an antibody. The polyclonal antibody can be prepared by an immunization method such as a lymph node injection method, a multi-site subcutaneous injection method, a multi-route combined injection method, etc. In the specific Examples of the present invention, the polyclonal antibody with high titer is finally obtained by immunizing a sheep with a proBDNF fragment (SEQ ID NO: 37) as an antigen mixed with Freund's adjuvant via multi-site subcutaneous injection at the back; and conducting an booster immunization.

The binding molecule that specifically binds to proBDNF according to the present invention has an alleviative or therapeutic effect on autoimmune diseases. Non-limiting exemplary autoimmune diseases include: rheumatoid arthritis, ankylosing spondylitis, psoriasis, systemic lupus erythematosus, mixed connective tissue disease, autoimmune diabetes mellitus (Type I Diabetes Mellitus), multiple sclerosis, aplastic anemia, etc. The uses of the binding molecule also include: mitigating neurologic impairment; inhibiting inflammatory cytokine infiltration in the central nervous system; alleviating myelin sheath loss in the spinal white matter; or reducing the expression of IL-1, IL-6, IL-17, IFN-γ or TNF-α.

The present invention further provides a pharmaceutical composition comprising an effective amount of the binding molecule. The composition can further comprise a pharmaceutically acceptable carrier. The pharmaceutical composition can be administered by a conventional route, including, but not limited to, intravenous, intraperitoneal injection, and the like. The pharmaceutical composition of the present invention can also be used in combination with other therapeutic agents for autoimmune diseases.

The term "pharmaceutically acceptable" as used in the present invention means that no adverse, allergic or other side effects will be generated when the binding molecule itself and the composition are suitably administered to an animal or a human. As used herein, a "pharmaceutically acceptable carrier" should be compatible with the binding molecule of the present invention, i.e., can be blended with the binding molecule, without greatly reducing the effect of the composition in general.

The term "effective amount" as described in the present disclosure refers to an amount sufficient to produce beneficial and desired results that include clinical results of alleviation of disease progression or cure of a disease. The "effective amount" can be achieved by one or more administrations. Specific dosages should be determined by the route of administration, the status of a patient and other factors, which are within the scope of skills of the skilled physicians.

Specific examples of some substances that can be used as pharmaceutically acceptable carriers or components thereof are saccharides such as lactose, glucose and sucrose; starches such as corn starch and potato starch; cellulose and derivatives thereof such as carboxymethylcellulose sodium, ethylcellulose and methylcellulose; tragacanth powder; malt; gelatin; talc; solid lubricants such as stearic acid and magnesium stearate; calcium sulfate; vegetable oils such as peanut oil, cottonseed oil, sesame oil, olive oil, corn oil and cocoa butter; polyols such as propylene glycol, glycerol, sorbitol, mannitol and polyethylene glycol; alginic acid; emulsifiers, such as Tween®; wetting agents such as sodium lauryl sulfate; colorants; flavoring agents; tableting agents; stabilizers; antioxidants; preservatives; pyrogen-free water; isotonic saline solutions; phosphate buffers, etc.

The composition of the present invention can be formulated into various dosage forms as desired and can be administered at a dosage beneficial to a patient which is determined by a physician based on factors such as the type, age, body weight and general disease condition of the patient, the mode of administration, etc. The mode of administration can be, for example, injection or other modes for treatment.

The binding molecule of the present invention can be used in an unseparated or separated form. In addition, the binding molecule of the present invention can be used alone or in a mixture comprising at least one binding molecule of the present invention (or a variant or fragment thereof). In other words, the binding molecules can be used in combination, for example, as a pharmaceutical composition comprising two or more binding molecules of the present invention, variants or fragments thereof. For example, binding molecules with different, but complementary activities can be combined in one therapeutic regimen to achieve the desired prophylactic, alleviative or therapeutic effect. Alternatively, binding molecules with the same activities can also be combined in one therapeutic regimen to achieve the desired prophylactic, alleviative or therapeutic effect.

The dosing regimen can be adjusted to provide the optimal desired response (e.g., a therapeutic response). The suitable dosage can be, for example, in the range of 0.1-100 mg/kg body weight, preferably 0.5-15 mg/kg body weight. In addition, for example, a single bolus can be given, or multiple separated doses can be given over time, or the dosage can be reduced or increased in proportion depending on the severity of the condition being treated. The binding molecule and composition of the present invention are preferably sterile. The methods for sterilizing these molecules and compositions are well known in the art.

Also disclosed herein are kits comprising the subject compositions. In some embodiments, the kit comprises a binding molecule which specifically binds to a precursor of brain-derived neurotrophic factor. In some embodiments, the binding molecule is an antibody, preferably a monoclonal antibody disclosed here. Non-limiting examples of such antibodies include those having a heavy chain variable region that comprises a CDR1 region as shown in SEQ ID NO: 1, a CDR2 region as shown in SEQ ID NO: 2 and a CDR3 region as shown in SEQ ID NO: 3; and a light chain variable region that comprises a CDR1 region as shown in SEQ ID NO: 4, a CDR2 region as shown in SEQ ID NO: 5 and a CDR3 region as shown in SEQ ID NO: 6a. Additional exemplary antibodies for packaging into a kit can include those antibodies having a heavy chain variable region shown in SEQ ID NO: 7; and the light chain variable region shown in SEQ ID NO: 8. Other suitable antibodies to be packaged into the subject kit may include those having a heavy chain shown in SEQ ID NO: 9; and the light chain shown in SEQ ID NO: 10.

In general, a subject kit can take the form of a container including but not limited to boxes, ampules, bottles, vials, tubes, bags, pouches, blister-packs, or other suitable container forms known in the art. Such containers can be made of plastic, glass, laminated paper, metal foil, or other materials suitable for holding medicaments. The subject kit typically includes user instructions printed in one or more multiple languages instructing users how to use the compositions contained therein. In some embodiments, the instruction comprises information of using the compositions of the kit for treating a subject suffering from any autoimmune disease disclosed herein.

The present invention will be further illustrated with reference to specific examples. It should be understood that these examples are for the purpose of illustrating the present invention only, rather than limiting the scope of the present invention. The experimental methods, for which specific conditions are not described in the following examples, are generally performed according to conventional conditions such as those described in J. Sambrook, et al. (eds)., Molecular Cloning: a Laboratory Manual, Third Edition, Science Press, 2002, or in accordance with the condition recommended by the manufacturer.

Example 1

Prokaryotic Expression of Human proBDNF Antigen 1.1 Construction and Identification of pET22b-proBDNF Vector A PCR amplification was performed with the cDNA of human tumor cell U87MG (purchased from RAYGENE Corporation) as a template using the following primers:

```
PROBDNF-F:
                                    (SEQ ID NO: 15)
5'GCGAATTCCCCATGAAAGAAGCAAACATCC3';
and PROBDNF-R:
                                    (SEQ ID NO: 16)
5'CCGCTCGAGTTATCTTCCCCTTTTAATGGTCAATG3'.
```

A PRO BDNF gene fragment (703 bp) with EcoRI/XhoI restriction sites at both ends was obtained and double-digested with EcoRI and XhoI (purchased from NEB Corporation) to obtain a target gene fragment, proBDNF. A vector plasmid pET22b (purchased from Novogen Corporation) was double-digested with EcoRI and XhoI, and a vector fragment was recovered after agarose gel electrophoresis. The vector fragment was ligated with the aforementioned target gene fragment proBDNF by T4 ligase (purchased from NEB Corporation), and then transfected into *E. coli* TOP10 (purchased from LIFE Corporation). A prokaryotic expression plasmid pET22b-proBDNF containing a correct human proBDNF gene sequence was obtained through ampicillin resistance screening, identification of a positive clone containing the insert by EcoRI/XhoI digestion, and verification by sequencing.

1.2 Expression and Purification of Human proBDNF Protein

The pET22b-proBDNF plasmid was transfected into an expression host strain BL21 (DE3) (purchased from Novagen Corporation), spread on a plate containing a culture medium supplemented with ampicillin, and cultured in an inverted position at 37° C. overnight. A monoclone was picked up for inducible expression, and then cultured under shaking until the $OD_{600}$ reached 0.6-0.8. IPTG was added to a final concentration of 1 mM, and the bacterial suspension was collected after 4 h induction at 30° C. The pellet was collected by centrifugation, and 1/10 volume of buffer A (50 mM $NaH_2PO_4$, 300 mM NaCl, 10 mM imidazole, pH 8.0) was added for re-suspension. PMSF was added (to a final concentration of 1 mM). The mixture was placed on ice, sonicated (for 3 seconds at an interval of 10 seconds, 99 times a round, a total of 4 rounds), and centrifuged (12,000 g at 4° C.) for 15 min, and then the supernatant was collected by centrifugation. The target expression protein was purified by chromatography on Ni—NTA Agarose (purchased from QIAGEN Corporation) affinity column, and then dialyzed against the PBS solution. The purity of the purified and dialyzed protein was analyzed on 12% SDS-PAGE, and the content of the protein was detected by A280. A small amount of the protein was run on SDS PAGE to detect its molecular weight. The SDS-PAGE results as shown in FIG. 1 indicate that the target band obtained by purification in lane 1 has a molecular weight of about 30 kD, which is substantially the same as the theoretical molecular weight of the proBDNF molecule (27.8 kD).

Example 2

Eukaryotic Expression of Human proBDNF Pro-Domain 2.1 Construction of Human proBDNF Pro-Domain Expression Vector V5F-Pro-Domain A PCR amplification was performed with the plasmid pET22b-proBDNF obtained above as a template using the following primers:

```
BDNFproVF1 (SEQ ID NO: 17):
5'GCTGGCTAGCACCCATGAAAGAAGCAAACATCCGAG3';
and

BDNFproVR1 (SEQ ID NO: 18):
5'CCGCTCGAGGTGGCGCCGGACCCTCATG3'.
```

A human proBDNF pro-domain gene fragment (350 bp) with NheI/XhoI restriction sites at both ends was obtained. The PCR fragment was double-digested with NheI and XhoI (purchased from NEB Corporation). The obtained pro-domain gene fragment was ligated, by T4 DNA ligase, with the vector V5F (purchased from RAYGENE Corporation) which was also double-digested with NheI and XhoI (purchased from NEB Corporation), and then transfected into host strain TOP10 (purchased from LIFE Corporation). A positive clone was picked up for PCR identification, and correct insertion was verified by sequencing. Then, a V5F-pro-domain plasmid was successfully constructed.

2.2 Expression and Purification of Human proBDNF Pro-Domain Protein

Well-grown HEK293F cells (HEK293F, purchased from LIFE Corporation) were seeded in a conical culture flask at a density of $1 \times 10^6$ cells/ml and cultured at 37° C., 5% $CO_2$ at 120 rpm overnight. The V5F-pro-domain plasmid obtained from the above procedure and a liposome (293Fectin, purchased from LIFE Corporation) were respectively diluted with DMEM, gently mixed, and incubated at room temperature for 20 min. The incubated DNA-liposome complex was added to HEK293F cells and cultured at 37° C., 5% $CO_2$ under 120 rpm for 72 h. The cell culture was collected and centrifuged at 4500 g for 15 min. The cells were removed to obtain the supernatant. 1 ml of FLAG antibody affinity filler (ANTI-FLAG Agarose Affinity Gel, purchased from Sigma-Aldrich Corporation) was loaded onto a column, and the FLAG affinity column was equilibrated with 5-10 column volumes of a lysis buffer (50 mM PB, 0.3 M NaCl, 5% glycerol). The centrifuged cell culture supernatant was passed through the FLAG affinity column at 1 ml/min, and the flow-through liquid was collected and stored at 4° C. The column was washed with 5-10 column volumes of wash buffer 1 (50 mM PB, pH 7.8, 0.3 M NaCl, 5% glycerol), and washout liquid 1 was collected and stored at 4° C. The column was washed with 4-5 column volumes of wash buffer 2 (50 mM PB, pH7.8, 0.5 M NaCl, 5% glycerol), and washout liquid 2 was collected and stored at 4° C. The column was eluted with 4-5 column volumes of elution buffer (50 mM Glycine. HCl, pH 3.0, 0.3 M NaCl, 5% glycerol), and the eluate was collected. After addition of a neutralizing buffer (1 M Tris. HCl, pH 8.0), the eluate was dialyzed against a dialysis solution (50 mM PB, pH 7.8, 0.3 M NaCl, 5% glycerol) at 4° C. overnight and stored. A small amount of the eluate was run on SDS PAGE. The results of electrophoresis as shown in FIG. 2 indicate that the target band in lane 1 has a molecular weight of about 20 kD, which is slightly larger than the theoretical molecular weight of the human proBDNF pro-domain protein (13 kD). Without being bound by theory, this may be related to the degree of glycosylation of the expressed target protein in the eukaryotic system.

Example 3

Eukaryotic Expression of Rat proBDNF Pro-Domain Fusion Protein (Rat proBDNF Pro-Domain-Fc)

3.1 Construction of Rat proBDNF Pro-Domain Fusion Expression Vector V5FC-rat-pro-domain-Fc A PCR amplification was performed with rat cDNA (purchased from RAYGENE Corporation) as a template using the following primers:

```
RatproF1:
                                    (SEQ ID NO: 19)
5'GCTGGCTAGCGCGCCCATGAAAGAAGCAAAC3';
and RatproR1:
                                    (SEQ ID NO: 20)
5'CCGCTCGAGGCGCCGAACCCTCATAGACATG3'.
```

A rat proBDNF pro-domain gene fragment (356 bp) with NheI/BamHI restriction sites at both ends was obtained. The PCR fragment was double-digested with NheI and BamHI (purchased from NEB Corporation). The obtained pro-domain gene fragment was ligated, by T4 DNA ligase, with the Fc fusion expression vector VSFC (Purchased from RAYGENE Corporation) which was also double-digested with NheI and BamHI (purchased from NEB Corporation), and transfected into host strain TOP10 (purchased from LIFE Corporation). A positive clone was picked up for PCR identification, and correct insertion was verified by sequencing. Then, a VSFC-rat-pro-domain plasmid was successfully constructed.

3.2 Expression and Purification of Rat proBDNF Pro-Domain Fusion Protein

Well-grown HEK293F cells (HEK293F, purchased from LIFE Corporation) were seeded in a conical culture flask at a density of $1\times10^6$ cells/ml and cultured at 37° C., 5% $CO_2$ under 120 rpm overnight. The VSFC-rat-pro-domain plasmid obtained from the above procedure and a liposome (293Fectin, purchased from LIFE Corporation) were respectively diluted with DMEM, gently mixed, and incubated at room temperature for 20 min. The incubated DNA-liposome complex was added to HEK293F cells and cultured at 37° C., 5% $CO_2$ under 120 rpm for 72 h. The cell culture was collected and centrifuged at 4500 g for 15 min. The cells were removed to obtain the supernatant. 1 ml of proteinA affinity filler (proteinA Agarose, purchased from RAYGENE Corporation) was loaded onto a column, and the proteinA affinity column was equilibrated with 5-10 column volumes of a lysis buffer (50 mM PB, 0.3 M NaCl, 5% glycerol). The centrifuged cell culture supernatant was passed through the proteinA affinity column at 1 ml/min, and the flow-through liquid was collected and stored at 4° C. The column was washed with 5-10 column volumes of PBS (20 mM PB, pH 7.8, 0.15M NaCl), and washout liquid 1 was collected and stored at 4° C. The column was eluted with 4-5 column volumes of elution buffer (100 mM Glycine. HCl, pH 2.5), and the eluate was collected. After addition of 10% by volume of a neutralizing buffer (1 M Tris. HCl, pH 8.0), the eluate was dialyzed against a dialysis solution (50 mM PB, pH 7.8, 0.3 M NaCl, 5% glycerol) at 4° C. overnight and stored. A small amount of the eluate was run on SDS PAGE. The results of electrophoresis as shown in FIG. 3 indicate that the target band in lane 1 has a molecular weight of about 44.3 kD (indicated by the arrow), which is comparable to the theoretical molecular weight of the rat proBDNF pro-domain fusion protein (rat proBDNF pro-domain-Fc).

Example 4

Preparation and Identification of Anti-Human proBDNF Pro-Domain Monoclonal Antibody 4.1 Immunization with a Recombinant Protein 1 ml of the purified human proBDNF protein (1.0 mg/mL) obtained in Example 1 above as an antigen was fully mixed and emulsified with 1 mL Freund's Complete Adjuvant (purchased from Sigma-Aldrich Corporation), and then used to subcutaneously immunize 6- to 8-week-old BALB/c mice, wherein each mouse was immunized with 100 μg of the human proBDNF antigen. After 4 weeks, the human proBDNF antigen was mixed and emulsified with Freund's Incomplete Adjuvant, and used to immunize the mice by intraperitoneal injection of 50 μg each mouse. Thereafter, booster immunization was conducted by intraperitoneal injection of 50 μg of the antigen at an interval of 2 weeks. One week after the fourth booster immunization, the antiserum titer of the mice was measured by an ELISA method using a plate coated with the purified human proBDNF pro-domain protein obtained in Example 2 above. The booster immunization was continued until the antiserum titer of the mice reached $>10^5$. 3 weeks after the last booster immunization, 20 μg of the human proBDNF pro-domain protein above was used for immunization within the spleen.

4.2 Construction of Human proBDNF Hybridoma Cell Strains 4 days after the booster immunization within the spleen, the spleens were removed from the mice aseptically. Lymphocytes were separated by filtration through a 100-mesh screen and fused with myeloma cell line SP2/0. After selective culture on hypoxanthine, aminopterin and thymidine (HAT) for 3 days, HT medium was added for additional culture for 1 week. Positive clones were screened by ELISA using a plate coated with the human proBDNF of the above examples of the present invention as an antigen. Subcloning was performed three times by a limited dilution method and the subclones were continuously cultured for 2 months. Finally, stable hybridoma cell lines were obtained and the clones were designated as: 2B11, 2C7, 5C10, 4C3, 6F3, 2F3, 8E1, and 1G7.

4.3 Purification of Antibodies

Above hybridoma cell clones were injected intraperitoneally into mice in respective groups at an amount of $5\times10^5$ cells/mouse to prepare ascites. 100 ml of ascites was diluted with 2× volume of 0.06 M sodium acetate buffer, pH 4.0, and 4% octanoic acid was slowly added dropwise with stirring. After stirring for 30 min, the turbid solution was centrifuged at 10,000 g for 30 min. The precipitate was discarded and the supernatant was dialyzed against 0.01 M phosphate buffer, pH 7.4 overnight. An equal volume of saturated ammonium sulfate was added to the dialysate slowly, followed by standing for 2 hours. The turbid solution was centrifuged at 10,000 g for 10 min. The supernatant was discarded and the precipitate was dissolved with a 0.01 M PBS, pH 7.4. The solution was dialyzed against 0.01 M PBS, pH 7.4, with 2× buffer exchange at an interval of no less than 5 hours. The dialysate was centrifuged at 10,000 g for 10 min. The precipitate was discarded and the supernatant was collected.

A protein G affinity column (purchased from GE Corporation) was recovered at room temperature, and equilibrated with 5 column volumes of PBS (0.01 M PB, 0.15 M NaCl, pH 7.4). The supernatant collected in the above paragraph was loaded onto the column. The column was washed with 5 column volumes of PBS, and eluted with 0.1 M glycine hydrochloride solution, pH 2.3. 1/10 volume of 1 M disodium hydrogen phosphate solution, pH 9.0 was added to the eluate for neutralization. The solution was dialyzed against 0.01 M PBS, pH 7.4, with 2× buffer exchange at an interval of more than 5 hours. The dialysate was centrifuged at 10,000 g for 10 min, and the supernatant was filtered through a 0.22 μm filter for storage to obtain purified monoclonal antibodies corresponding to respective clones.

4.4 Identification of the Binding Regions of Monoclonal Antibodies with ELISA

Experimental group 1: The purified human proBDNF protein obtained in Example 1 was diluted with PBS (0.01 M PB, 0.15 M NaCl, pH 7.4). Each group comprised 8 wells, to which would be added 8 corresponding purified monoclonal antibodies, respectively.

Experimental group 2: The purified human proBDNF pro-domain protein obtained in Example 2 was diluted with PBS (0.01 M PB, 0.15 M NaCl, pH 7.4). Each group comprised 8 wells, to which would be added 8 corresponding purified monoclonal antibodies, respectively.

The proteins diluted in experimental groups 1 and 2 were used for coating overnight at 4° C. in a volume (mass) of 50 μl (50 ng), respectively. The supernatant was then discarded, and each well was washed twice with PBS and blocked with 5% milk powder in PBS at 37° C. for 2 hours. The eight purified monoclonal antibodies, each 50 μl (1 μg/ml), obtained in above Example 3.3 were then added to 8 wells of experimental groups 1 and 2, respectively, and incubated at 37° C. for 1 hour. The plate was washed three times with PBST containing 0.5% Tween-20, and then 50 μl HRP-labeled goat anti-mouse secondary antibody was added and incubated at 37° C. for 1 hour. The plate was washed five times with PBST containing 0.5% Tween-20, an ABTS substrate was added for development for 15 minutes, and absorbance values were measured at 405 nm by a microplate reader. The experiment was repeated twice, and the absorbance values measured in duplicate were averaged. An absorbance value of more than three times greater than the reading of the negative control well was determined to be positive.

As shown in FIG. 4, the purified monoclonal antibody 2B11 binds to both the human proBDNF and the human proBDNF pro-domain, suggesting that the antibody 2B11 binds to the common segment of the two proteins, i.e., the human proBDNF pro-domain region.

4.5 Horseradish Peroxidase Labeling of Monoclonal Antibody 2B11

10 mg of horseradish peroxidase (HRP) was dissolved in 1 ml of water, and 1 ml of 0.5 M $NaIO_4$ was added to allow for reaction at 4° C. for 30 min. 1 ml of 0.16 M ethylene glycol was added, and reacted at 4° C. for 30 min. 10 mg of 2B11 antibody was dialyzed against 0.05 M carbonate buffer, pH 9.5. The oxidized HRP was well mixed with the 2B11 antibody and dialyzed at 4° C. overnight. 0.4 ml of 1 mg/ml $NaBH_4$ was added and stirred at 4° C. for 2 h. pH was adjusted to a weak acidity with a low concentration of $NaH_2PO_4$ solution, and an equal volume of glycerol was added for storage until use.

4.6 Determination of the Species Specificity of Antibody 2B11 Binding to proBDNF with ELISA Experimental group 1: The purified human proBDNF protein obtained in example 1 was diluted with PBS (0.01 M PB, 0.15 M NaCl, pH 7.4).

Experimental group 2: The prokaryotically expressed mouse proBDNF (purchased from Alomone Labs Corporation) was diluted with PBS (0.01 M PB, 0.15 M NaCl, pH 7.4).

Experimental group 3: The eukaryotically expressed rat proBDNF pro-domain obtained in example 3 was diluted with PBS (0.01 M PB, 0.15 M NaCl, pH 7.4).

The proteins diluted in experimental groups 1, 2 and 3 were used for coating overnight at 4° C. in a volume (mass) of 50 μl (50 ng), respectively. The supernatant was then discarded, and each well was washed twice with PBS and then blocked with 5% milk powder in PBS at 37° C. for 2 hours. The supernatant was discarded, and 50 μl of the diluted HRP-labeled 2B11 antibody in Example 4.5 (1 μg/ml) was added and incubated at 37° C. for 1 hour. The supernatant was discarded and each well was washed three times with PBST containing 0.5% Tween-20. An ABTS substrate was added for development for 15 minutes and absorbance values were measured at 405 nm by a microplate reader. An absorbance value of more than three times greater than the reading of the negative control well was determined to be positive.

As shown in FIG. 5, the antibody secreted from clone 2B11 binds to both the human proBDNF protein and the mouse proBDNF protein prepared in example 1 of the present invention and the eukaryotically expressed rat proBDNF pro-domain in example 3.

4.7 Determination of the Antibody Subtype of Clone 2B11 with ELISA

Figure 6:
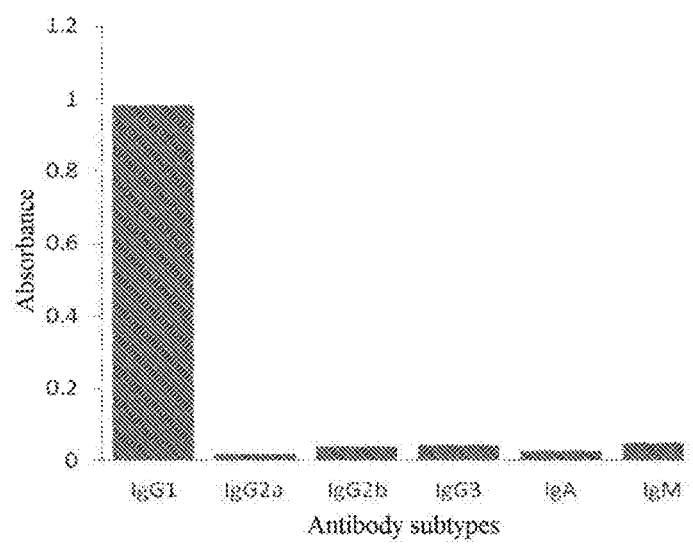
FIG. 6 shows the results of the subtype analysis of anti-proBDNF monoclonal antibody 2B11 in Example 3 of the present invention.

Six experimental groups were established based on the number of antibodies to be typed. The diluted prokaryotically expressed human proBDNF (50 ng) protein was added to each well in each group in a volume of 50 μl, and used for coating overnight at 4° C. The supernatant was discarded, and each well was washed twice with PBS (0.01 M PB, 0.15 M NaCl, pH 7.4) and blocked with 5% milk powder in PBS at 37° C. for 2 hours. The supernatant was discarded, and 50 μl of the above purified and diluted antibody from clone 2B11 (1 μg/ml) was added to each well and incubated at 37° C. for 1 hour. The supernatant was discarded and each well was washed three times with PBST containing 0.5% Tween-20. Six corresponding typing antibodies (purchased from Sigma-Aldrich Corporation): goat anti-mouse IgG1, goat anti-mouse IgG2a, goat anti-mouse IgG2b, goat anti-mouse IgG3, goat anti-mouse IgA, and goat anti-mouse IgM, were added to experimental groups 1-6, respectively, and incubated at 37° C. for 1 hour. The supernatant was discarded and each well was washed three times with PBST containing 0.5% Tween-20. 50 μl of HRP-labeled donkey anti-goat secondary antibody was added and incubated at 37° C. for 1 hour. The supernatant was discarded and each well was washed five times with PBST containing 0.5% Tween-20. An ABTS substrate was added for development for 15 minutes and absorbance values were measured at 405 nm by a microplate reader. An absorbance value of more than three times greater than the reading of the negative control well was determined to be positive. As shown in FIG. 6, clone 2B11 was identified as an IgG1 type.

Example 5

Sequencing of Monoclonal Antibody 2B11

The sequence of 2B11 was cloned by the 5'-RACE method and determined by sequencing (please refer to the Takara 5'-full RACE Kit instructions for specific procedure): The exposed 5' phosphate groups in total RNA were dephosphorylated with alkaline phosphatase (CTAP). The amount of total RNA used was 2 μg; and the total RNA was recovered by phenol/chloroform extraction after the reaction. The 5' cap structure of mRNA was removed with Tobacco Acid Pyrophosphatase (TAP), with one phosphate group preserved. A 5' RACE Adaptor was ligated to the mRNA with T4 RNA ligase, and the product was recovered by phenol/chloroform extraction after the reaction. A reverse transcription reaction was performed using a reverse transcriptase, and the primers used were Random 9mers provided in the Kit.

The target gene was PCR amplified with the reverse transcription product as a template using a high fidelity enzyme and the following primers:

```
5': 5' RACE Outer Primer:
                                 (SEQ ID NO: 21)
CATGGCTACATGCTGACAGCCTA;

3': Heavy chain: mIgG1-out primer:
                                 (SEQ ID NO: 22)
CCAGAGTTCCAGGTCACTGTCACT;

Light chain: mκ-out primer:
                                 (SEQ ID NO: 23)
AGGTGCTGTCTTTGCTGTCCTG.
```

A Nested PCR was performed with the PCR product obtained by the above amplification as a template using the following primers:

```
5': 5'RACE Inner Primer:
                                 (SEQ ID NO: 24)
CGCGGATCCACAGCCTACTGATGATCAGTC GATG;

3': Heavy chain: mIgG1-inner primer:
                                 (SEQ ID NO: 25)
CCAGGGTCACCATGGAGTTAGTTT;

Light chain: mκ-inner primer:
                                 (SEQ ID NO: 26)
GTTCAAGAAGCACACGACTGAGG.
```

The PCR product obtained by the above amplification was purified and TA-cloned (pGEM-T Easy Vector Kit, purchased from Promega Corporation, see the Kit instructions for the procedure) to give Teasy-2B11VH and Teasy-2B11VK vectors, respectively. The heavy and light chain sequences of monoclonal antibody 2B11 were obtained by sequencing, and shown in SEQ ID NO: 9 and SEQ ID NO: 10, respectively. The heavy chain variable region and light chain variable region sequences were determined according to KabatMan and shown in SEQ ID NO: 7 and SEQ ID NO: 8, respectively. The sequences of the CDR1, CDR2 and CDR3 of the heavy chain variable region were determined according to the Kabat numbering rule and shown in SEQ ID NOs: 1-3, respectively, and the sequences of the CDR1, CDR2 and CDR3 of the light chain variable region were determined and shown in SEQ ID NOs: 4-6, respectively.

Example 6

Construction and Preliminary Identification of Binding Activity of Chimeric Antibody Vectors pH-CH2B11 and pK-CH2B11

6.1 Construction of Vector pH-CH2B11

A PCR amplification was performed with the vector Teasy-2B11VH constructed in example 5 of the present invention as a template using the following primers:

```
2BVHF:
                                 (SEQ ID NO: 27)
5'-ggctgttcacagcctttcctggtttcctgtctgaggtgaaggtgg tggag-3';

2BVHR:
                                 (SEQ ID NO: 28)
5'-cgatgggcccttggtggaggctgaggagacggtgactg-3'.
```

The heavy chain variable region of 2B11 antibody was obtained.

Simultaneously, a PCR amplification was performed with the antibody vector pH-EGFRvIII (i.e., pH-CH12, see example 7.1 of PCT/CN2009/074090 for the method for constructing the vector) as a template:

```
Primer FcF:
                                 (SEQ ID NO: 29)
  5'-gcctccaccaagggcccatcg gtcttccccctgg-3';
and Primer PIHR:
                                 (SEQ ID NO: 30)
  5'-cgcttttgagagggagtactcac-3'.
```

The constant region of human IgG1 was obtained.

The two PCR amplified fragments above were bridged after recovery and PCR amplified using the following primers: Nhe: 5'-cctagctagccaccatgagagtgctgattcttttgt ggctgt-tcacagcctttcct-3' (SEQ ID NO: 31); and the above primer PIHR (SEQ ID NO: 30). The product was recovered on agarose gel, double-digested with NheI and NotI (purchased from NEB Corporation), and ligated into vector pH that was similarly double-digested to obtain the expression plasmid pH-CH2B11 containing a chimeric 2B11 heavy chain, which was confirmed by PCR and sequencing.

6.2 Construction of Vector pK-CH2B11

A PCR amplification was performed with the Teasy-2B11VK constructed in example 5 of the present invention as a template using the following primers:

```
2BVκF:
                                 (SEQ ID NO: 32)
5'-cttgcattcttgttgctttggtttccaggtgcaagatgtgacatcc agatgactc-3';
and 2BVκR:
                                 (SEQ ID NO: 33)
5'-agccaccgtacg ttttatttccaactttg-3'.
```

The light chain variable region of monoclonal antibody 2B11 was obtained and the fragment was recovered. The above PCR amplified fragment was amplified using the following primers: Eco:

```
                                        (SEQ ID NO: 34)
5'-gatcgatatccaccatggacatgatggtccttgctcagtttcttg cattcttgttg-3',
and (SEQ ID NO: 31)
2BVκR.
```

The amplified product was recovered on agarose gel, double-digested with EcoRV and BsiW1 (purchased from NEB Corporation), and ligated into vector pK that was similarly double-digested to obtain the expression plasmid pK-CH2B11 containing a chimeric 2B11 light chain, which was confirmed by PCR and sequencing.

Example 7

Construction and Identification of Binding Activity of Chimeric Antibody CH2B11

The expression vectors pH-CH2B11 and pK-CH2B11 constructed above were co-transfected into CHO cells in suspension for expression, and the culture supernatant was collected after 3 days. The culture supernatant of the CHO cells contained the expressed chimeric antibody CH2B11.

The culture supernatant was used to perform an ELISA binding experiment. The experimental method was substantially the same as the method of Example 4.4 of the present invention except that only experimental group 1 using the human proBDNF protein prepared in Example 1 of the present invention was included, and then serial dilutions of the cell supernatant in this example, instead of the corresponding eight monoclonal antibody clones, were added to the wells. Likewise, an absorbance value of three times greater than the reading of the negative control well was determined to be positive.

Figure 7:
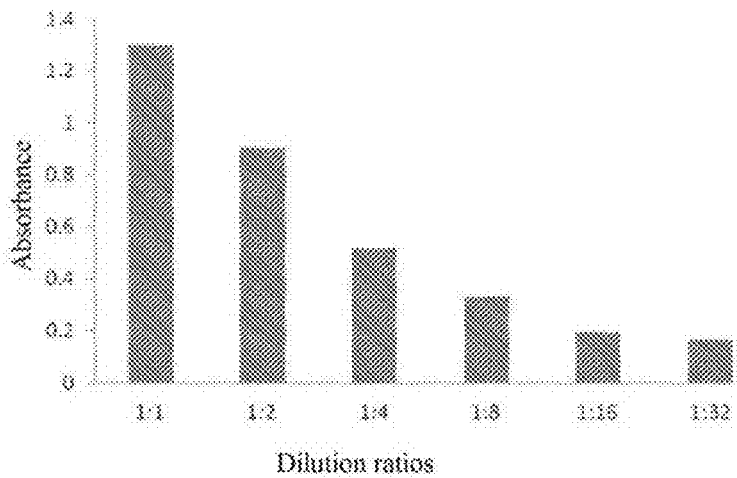
FIG. 7 shows binding of the human-mouse chimeric antibody CH2B11 of Example 6 of the present invention to the human proBDNF protein of Example 1 of the present invention under different dilution conditions.

The experiment results are shown in FIG. 7. The culture supernatant of CHO cells secreting the chimeric antibody CH2B11 still shows an activity of binding to human proBDNF at 1:32 dilution, i.e., the binding property of the antibody is excellent.

Example 8

Monoclonal Antibody 2B11 Alleviates Clinical Symptoms of Mouse Model of Rheumatoid Arthritis Rheumatoid arthritis (RA) is a systemic autoimmune disease with unknown etiology, which mostly occurs in middle and old aged women and mainly involves joints. Joint symptoms are generally recurrent. With the increase in the number of onset, joint damages are increasingly serious, and ultimately lead to different degrees of dysfunction and deformity. More than 9 million visits and more than 250 thousand hospitalizations are caused by RA per year. The loss of labor capacity caused by RA leads to a huge economic loss and a heavy burden on family. The most commonly used RA mouse model is an arthritis model caused by collagenase injection (CAIA model). In this example, a CAIA model was used to evaluate the therapeutic effects of 2B11 on RA.

1. Experimental Animals 6- to 8-week-old female SPF-grade Balb/C mice, weighed 18-20 g (provided by the Department of Laboratory Animals, Central South University), were used in this experiment. Feeding conditions were as follows: clean grade, 5-6 mice/cage, water and feed ad libitum; the mouse food was given after being macerated in feeding water. The experimental animals were completely randomized.

Experiments were randomized into four groups:
(1) Normal control group: normal mice, no modeling;
(2) CAIA group: an autoimmune arthritis model was established, but PBS was given as a control treatment;
(3) CAIA+2B11 pretreatment group: monoclonal antibody 2B11 was intraperitoneally injected at 500 μg/kg once a day, with a total course of 1 week, from the day of modeling to day 7 after modeling;
(4) CAIA+2B11 treatment group: monoclonal antibody 2B11 was given 17 days after modeling.

2. Preparation of CAIA Model

A CAIA model was established by intraperitoneal injection of a collagenase antibody complex (consisting of 7 antibody complexes) from Modiquest Corporation, Netherlands (day 0 of modeling). 2.8 mg of the antibody complex was dissolved in 200 μl of PBS, and intraperitoneally injected directly. On day 3 of modeling, 25 μg of LPS (Sigma Corporation) was intraperitoneally injected again to promote the inflammatory response. In the normal control group, an equal volume of PBS was given on day 0 and day 3 of modeling. In the pretreatment group, the monoclonal antibody 2B11 (the 2B11 pretreatment group) was injected intraperitoneally at 500 μg/kg every day for one week from day 7 of modeling. In the treatment group, the monoclonal antibody 2B11 was injected intraperitoneally at 500 μg/kg for one week from day 17 after successful modeling.

3. Observation Indexes (1) Body weight measurement of animals: the body weight of animals can be reduced after the modeling of autoimmune arthritis (i.e., intraperitoneal injection of multiple antibody complexes). The body weight measurement of animals has become a very important index for evaluating the efficacy of a drug.

(2) Arthritis severity scoring: the degree of arthritis can be scored based on the number of joints involved, which is the most important index for evaluating the therapeutic effects of a drug on autoimmune arthritis.

(3) Degree of joint swelling: the thickness of soles was measured by a vernier caliper to evaluate the degree of joint swelling. The degree of joint swelling is also an important index for evaluating the process of arthritis and the efficacy of a drug.

Figure 8:
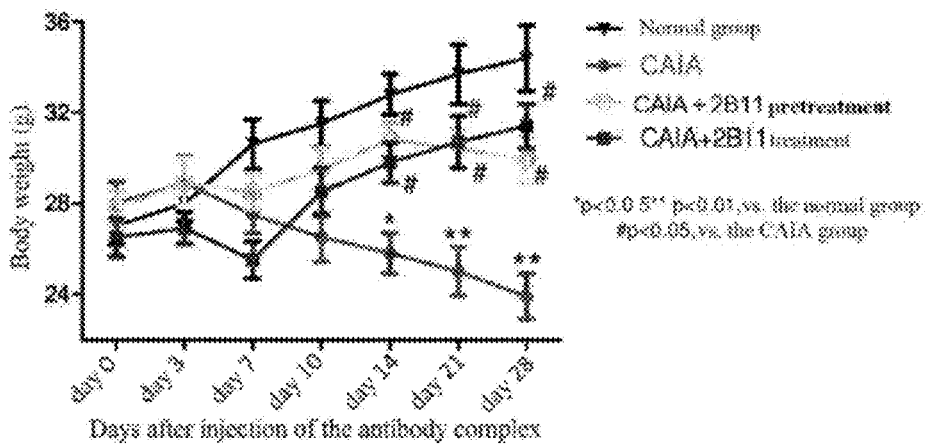
FIG. 8 shows the effect of intraperitoneally injected 2B11 on the body weight of Balb/C mice with autoimmune arthritis induced by collagenase (CAIA model) compared to the normal group.

4. Experimental Results (1) The effects of 2B11 on the body weights of mice with autoimmune arthritis are shown in FIG. 8. As compared to the normal group, the body weights of mice in the CAIA group were decreased continuously after the intraperitoneal injection of the collagenase antibody complex. (*, p<0.05, vs. the normal group; **, p<0.01, vs. the normal group). The degree of decline in the body weights of mice in the CAIA+2B11 pretreatment group or the CAIA+2B11 treatment group is significantly lower than that in the control group, which is statistically significant (#, p<0.05, the 2B11 group vs. the control group) (One-way variance analysis was performed using repeated measurements, and Tukey post-hoc test was used as a post hoc test analysis). This suggests that both pretreatment with 2B11 and administration of 2B11 after onset of the disease can significantly reduce the degree of decline in the body weights of arthritis mice.

(2) Effects of 2B11 on the arthritis severity of mice with autoimmune arthritis: After modeling, swelling and other symptoms could occur at small joints of mice. A common arthritis severity scoring method (see Table 1) was used to evaluate the preventive (the pretreatment group) and therapeutic (the treatment group) effects of 2B11 on autoimmune arthritis.

TABLE 1

| The number of joints involved | Arthritis score |
|---|---|
| swelling of 1-2 toes | 0.25 |
| swelling of 3-4 toes | 0.50 |
| slight swelling of soles or ankle joints | 0.50-0.75 |
| swelling of soles or ankle joints | 1.00 |
| swelling of soles or ankle joints + swelling of 1-2 toes | 1.25-1.50 |
| swelling of soles + ankle joints + toes | 2.00 |

Figure 9:
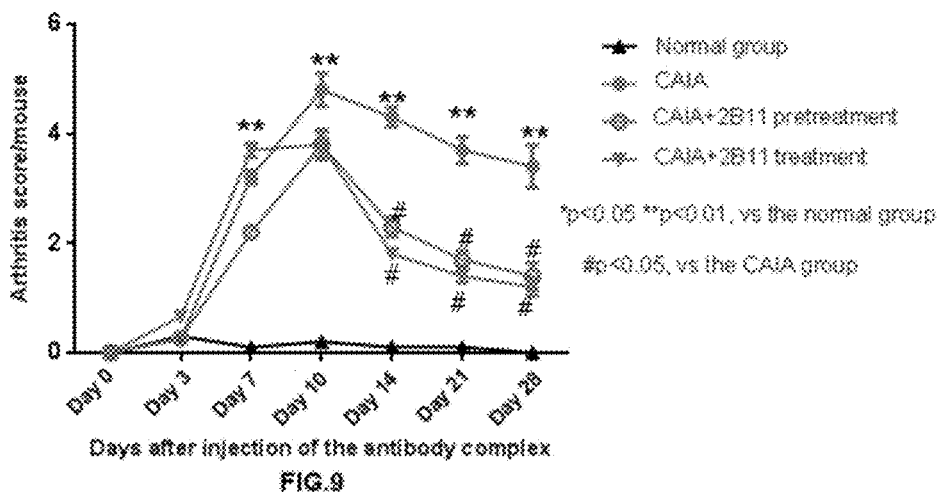
FIG. 9 shows the effect of intraperitoneally injected 2B11 on the arthritis scoring index of Balb/C mice with autoimmune arthritis induced by collagenase (CAIA model) compared to the normal group.

As shown in FIG. 9, no swelling occurred in the joints of mice in the normal group throughout the experiment, so the arthritis score was 0. In the CAIA group, swelling of various small joints and ankle joints occurred from day 7 of modeling and the arthritis score was increased significantly with the highest peak up to 4.8 points (day 10 after modeling). The arthritis scores of the mice in both the CAIA+2B11 pretreatment group and the CAIA+2B11 treatment group were significantly lower than that in the control group, although still higher than the normal group (One-way variance analysis was performed using repeated measurements, and Tukey post-hoc test was used as a post hoc test analysis). This suggests that 2B11, whether as a pretreatment or a treatment, can effectively alleviate the symptoms of mice with autoimmune arthritis.

Figure 10:
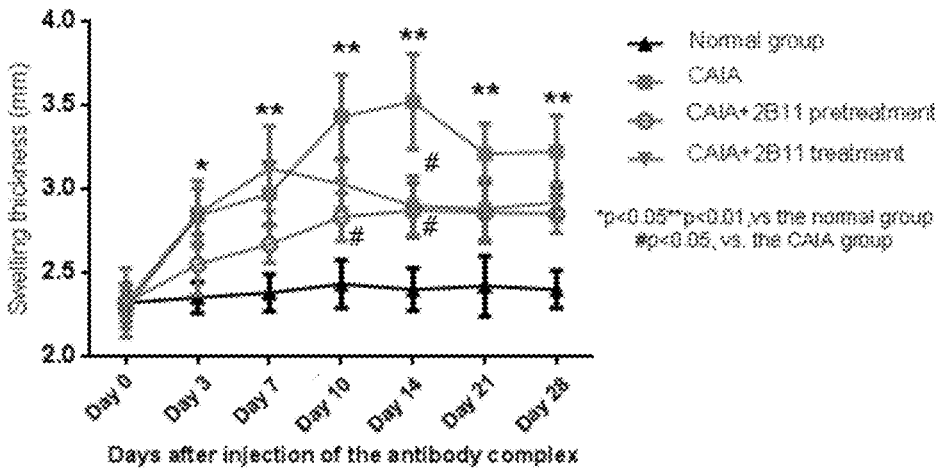
FIG. 10 shows the effect of intraperitoneally injected 2B11 on the degree of joint swelling of Balb/C mice with autoimmune arthritis induced by collagenase (CAIA model) compared to the normal group.

(3) Effects of 2B11 on joint swelling degree of mice with autoimmune arthritis: the soles in different groups were measured by using a vernier caliper to evaluate the degree of joint swelling of the mice. As shown in FIG. 10, the thickness of soles of mice in the control group was significantly increased as compared to the normal group, and the thickness of soles in the CAIA+2B11 pretreatment group and the CAIA+2B11 treatment group was significantly decreased as compared to the control group (*p<0.05, vs. the normal group; **p<0.01, vs. the normal group; #p<0.05, vs. the experimental group).

Example 9

Monoclonal Antibody 2B11 Alleviates Clinical Symptoms of Mice with Experimental Allergic Encephalomyelitis Experimental allergic encephalomyelitis (EAE) is a mouse model of clinical multiple sclerosis, which is considered to be an autoimmune disease predominantly mediated by specifically sensitized CD4+ T cells and characterized by mononuclear cell infiltration and demyelination around the small blood vessels in the central nervous system.

1. Experimental Animals 6- to 8-week-old female SPF-grade C57BL/6 mice, weighed 18-20 g (provided by the Department of Laboratory Animals, Central South University), were used in this experiment. Feeding conditions were as follows: clean grade, 5-6 mice/cage, water and feed ad libitum; the mice with a paralysis level of 3 or more and the dying mice were housed in a single cage during the experiment; and the mouse food was given after being macerated in feeding water. The experimental animals were completely randomized.

2. Preparation of EAE Model

The mice were anesthetized with sevoflurane. The completely emulsified MOG35-55 (3 mg/ml)/CFA (H37RA, 4 mg/ml) was subcutaneously injected into the left and right sides of the upper back and the left root of the tail of the mice at a dose of 150 μl/mouse. In addition, the mice were intraperitoneally injected with pertussis toxin PTX (0.5 μg/100 μl) at a dose of 50 μl/mouse, and were injected again with the same dose of PTX after 48 hours. On day 7, MOG35-55 (3 mg/ml)/CFA (H37RA, 2 mg/ml) was subcutaneously injected into the left and right sides of the lower back and the right root of the tail of the immunized mice at a dose of 150 μl/mouse.

3. Grouping of Animals and Administration

The mice were randomized into three groups, 10 mice per group:
(1) normal group (Normal);
(2) model group (EAE+NSS): 8 days after modeling, an equal volume of normal sheep serum was intraperitoneally injected at a dose of 0.2 ml/mouse each day for 7 consecutive days;
(3) model+anti-proBDNF antibody treatment group (EAE+anti-proBDNF): 9 days after modeling, when the EAE model mice were at the early stage of the disease, the mice began to receive treatment with intraperitoneally injected anti-proBDNF polyclonal antibody once a day for 7 consecutive days (2.5 mg/kg, 0.2 ml/mouse/day).

4. Observation Indexes (1) Clinical scoring of the EAE model: after modeling, clinical scoring was performed every day. The scoring criteria were as follows: 0, no clinical symptoms; 0.5, weakness of tail; 1, paralysis of tail; 2, loss of coordination movement; 2.5, paralysis of a unilateral hind limb; 3, paralysis of bilateral hind limbs; 3.5, paralysis of bilateral hind limbs with weakness of a forelimb; 4, paralysis of a forelimb; 5, dying or death. The score was recorded as 5 on the day when the mouse was found to be dead, and the score was no longer recorded from the next day.

5. Experimental Results

Figure 11:
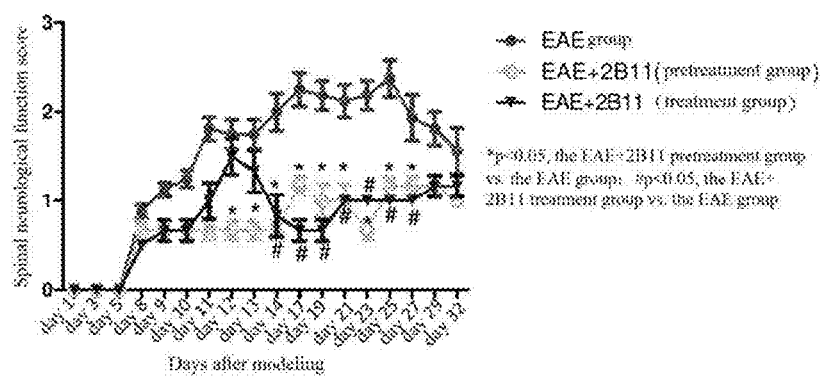
FIG. 11 shows the therapeutic effect of intraperitoneally injected 2B11 on the neurological function of mice with experimental allergic encephalomyelitis induced by injection of CFA/*Mycobacterium tuberculosis* compared to the EAE group.

As shown in FIG. 11, the clinical score of the mice in the EAE group began to significantly increase from day 7 after modeling, until day 32 after modeling. The score of the EAE+2B11 pretreatment group was significantly lower than that of the EAE group at the same time points during the period of day 7 to day 25 after modeling. This indicates that administration of 2B11 prior to onset of the disease can prevent and reduce the impaired spinal function caused by EAE. The score of the EAE+2B11 treatment group was significantly lower than that of the EAE group during the period of day 17 to day 29 after modeling. It is further indicated that administration of 2B11 has a good therapeutic effect even after onset of the disease.

Example 10

Preparation of Anti-proBDNF Polyclonal Antibody

A polyclonal antibody was prepared using the human proBDNF antigen having the following amino acid sequence:

(SEQ ID NO: 37)
APMKEANIRGQGGLAYPGVRTHGTLESVNGPKAGSRGLTSLADTFEHVIE

ELLDEDQKVRPNEENNKDADLYTSRVMLSSQVPLEPPLLFLLEEYKNYLD

AANMSMRVRR.

The preparation was specifically as follows.

(1) A human proBDNF fragment was amplified by PCR

```
(reverse primer:
'CTAGCGCCGAACCCTCATAGA-3' (SEQ ID NO: 35);

forward primer:
5'-TTAGCGCCGAACCCTCATAGA-3' (SEQ ID NO: 36)),
``` and cloned into the multiple cloning site of the vector pET100/D-TOPO (Invitrogen). The plasmid was transfected into *E. coli* BL21 for culturing. The bacterial colonies were grown in 1,000 ml of LB containing 100 µg/ml ampicillin at 37° C. with shaking at 300 rpm. Once the OD value of the culture measured at 580 nm reached 0.8, IPTG was added to a final concentration of 0.5 mM. The culture was incubated at 30° C. overnight, and then centrifuged at 11,000 g at 4° C. The bacteria were collected after 20 minutes. The bacterial plaque was suspended in 40 ml of 50 mM potassium phosphate buffer containing 0.3 M sodium chloride, 10% glycerol, 0.005% Triton-X 100, 10 mM imidazole, 1 mM DTT and 1 mM PMSF. The lysozyme was added to the solution to a final concentration of 0.2 mg/ml, and the solution was placed on ice for 25 minutes to lyse the cells. Then, the solution was sonicated 10 times, 30 s each, at a power of 50 W, and the whole reaction process was conducted on ice. The solution was again centrifuged at 11,000 g at 4° C. for 20 minutes. The resulting precipitate was placed in 50 ml of buffer I (consisting of 20 mM Tris (pH 8.0) supplemented with 0.2 M sodium chloride and 1% sodium deoxycholate), and well mixed on ice for 30 minutes. The resulting suspension was centrifuged at 3,000 g for 10 minutes, and the precipitate obtained by the centrifugation was placed into 50 ml of ice-cold buffer II (consisting of 10 mM Tris (pH 8.0) supplemented with 1 mM EDTA and 0.25% sodium deoxycholate). The resulting lysate was centrifuged again at 3,000 g for 10 minutes. The precipitate obtained by the centrifugation was washed three times with 40 ml of buffer II, and then dissolved in 40 ml of 8 M urea solution. The protein solution was centrifuged at 11,000 g at 4° C. for 25 minutes, and the resulting supernatant was added to a nickel column. When all of the supernatant flowed through, the nickel column was washed with a washing solution containing 8 M urea, 5 mM imidazole and 0.5 M sodium chloride. The OD value of the eluate was measured, and the washing was stopped until the OD value dropped to close to that of the washing solution. An eluting buffer containing 8 M urea, 1 M imidazole and 0.5 M sodium chloride was added to the nickel column to elute the target protein. The collected protein was separated by gel electrophoresis and then subjected to Coomassie brilliant blue staining. A solution consisting of 0.75 M L-arginine, 5 mM GSH (R), 0.5 mM GSSH (O), 5 mM EDTA and 0.1 M Tris (pH=9.5) was used to stabilize the protein of the eluate containing the target protein and neutralize the pH value of the eluate. The protein solution was dialyzed against 2 L of PBS at 4° C. for 4 hours, then against 5 L of PBS for 4 hours, and then against 10 L of PBS overnight.

(2) 2 ml of PBS containing 0.4% glutaraldehyde and 2 ml of Freund's Complete Adjuvant were successively added to 0.5 mg of the brain-derived neurotrophic factor precursor obtained in step (1) to form an emulsion. The emulsion was subcutaneously injected at multiple injection sites of the back and groin of an adult sheep. Subsequently, the emulsion was injected once every two weeks using a half dose of the antigen in Freund's Incomplete Adjuvant, until the antibody titer reached 1/10,000.

Example 11

Use of Anti-proBDNF Polyclonal Antibody in Early Stage of Experimental Autoimmune Encephalomyelitis (EAE)

1. Experimental Animals 6- to 8-week-old female SPF-grade C57BL/6 mice, weighed 18-20 g (provided by the Department of Laboratory Animals, Central South University) were used in this experiment. Feeding conditions were as follows: clean grade, 5-6 mice/cage, water and feed ad libitum; the mice with a paralysis level of 3 or more and the dying mice were housed in a single cage during the experiment, and the mouse food were given after being macerated in feeding water. The experimental animals were completely randomized.

2. Preparation of EAE Model

The mice were anesthetized with sevoflurane. The completely emulsified MOG35-55 (3 mg/ml)/CFA (H37RA, 4 mg/ml) was subcutaneously injected into the left and right sides of the upper back and the left root of the tail of the mice at a dose of 150 µl/mouse. In addition, the mice were intraperitoneally injected with pertussis toxin PTX (0.5 µg/100 µl) at a dose of 50 µl/mouse, and were injected again with the same dose of PTX after 48 hours. On day 7, MOG35-55 (3 mg/ml)/CFA (H37RA, 2 mg/ml) was subcutaneously injected into the left and right sides of the lower back and the right root of the tail of the immunized mice at a dose of 150 µl/mouse.

3. Grouping of Animals and Administration 30 mice were randomized into three groups, 10 mice per group:

(1) normal group (Normal);

(2) model group (EAE+NSS): 8 days after modeling, an equal volume of normal sheep serum was intraperitoneally injected at a dose of 0.2 ml/mouse each day for 7 consecutive days;

(3) model+anti-proBDNF antibody treatment group (EAE+anti-proBDNF): 9 days after modeling, when the EAE model mice were at the early stage of the disease, the mice began to receive treatment with intraperitoneally injected anti-proBDNF polyclonal antibody once a day for 7 consecutive days (2.5 mg/kg, 0.2 ml/mouse/day).

4. Experimental Post-Processing (1) Clinical scoring of the EAE model: after modeling, clinical scoring was performed every day. The scoring criteria are as follows: 0, no clinical symptoms; 0.5, weakness of tail; 1, paralysis of tail; 2, coordination movement disappears; 2.5, paralysis of a unilateral hind limb; 3, paralysis of bilateral hind limbs; 3.5, paralysis of bilateral hind limbs with weakness of a forelimb; 4, paralysis of a forelimb; 5, dying or death. The score was recorded as 5 on the day when the mouse was found to be dead, and the score was no longer recorded from the next day.

(2) HE staining & sectioning and pathological scoring.

The mice of 35 days after modeling (5 mice per group) were sacrificed through perfusion. The spinal cord was removed, and dehydrated, hyalinized, subjected to waxdip, made into a wax block, and sectioned (4 µm) for HE staining according to the conventional method. Infiltration of inflammatory cells was observed.

(3) LFB staining: the sections were stained according to the conventional LFB staining method, and the demyelination was observed.

(4) Detection of spinal cord disease-related gene expression:

The spinal cords of the mice of 35 days after modeling (5 mice per group) were detected by real-time PCR for the expression levels of proinflammatory cytokines IL-1, IL-6, IL-17, IFN-γ and TNF-α.

5. Analysis of Data

Graphpad prism software 5.0 was used for analysis. It is considered as significant difference if p<0.05.

Figure 12:
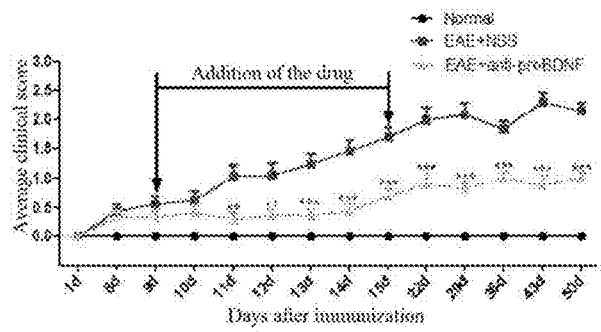
FIG. 12 shows the comparison of clinical scores of EAE model mice treated with NSS and an anti-proBDNF antibody respectively at the early stage of experimental autoimmune encephalomyelitis.

6. Results (1) Onset of the disease in the model mice: the neurologic impairment of the EAE model mice treated with the anti-proBDNF antibody was significantly reduced, and the clinical score after the treatment was basically stable at about 1 (FIG. 12).

Figure 13:
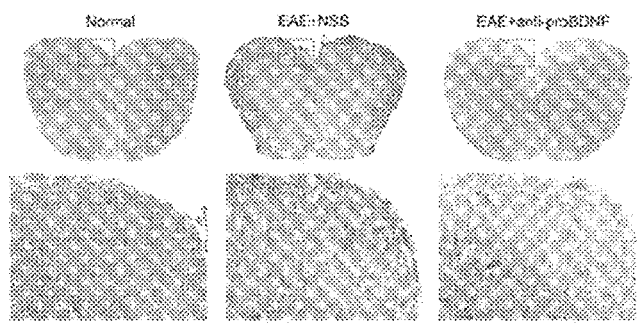
FIG. 13 shows the Hematoxylin and Eosin staining of spinal cords of EAE model mice treated with NSS and an anti-proBDNF antibody respectively at the early stage of experimental autoimmune encephalomyelitis.
Figure 14:
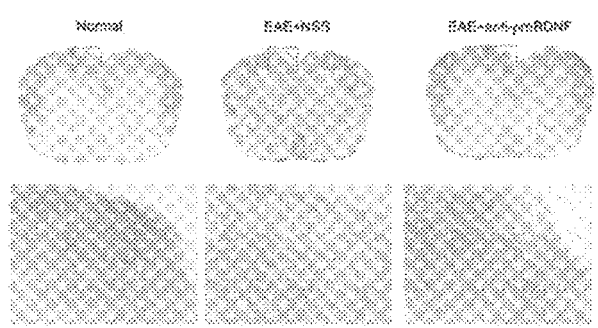
FIG. 14 shows the LFB staining of spinal cords of EAE model mice treated with NSS and an anti-proBDNF antibody respectively at the early stage of experimental autoimmune encephalomyelitis.

(2) Pathological section and pathological damage score: the results of light microscopy showed that the inflammatory cells in mice of the model group were densely distributed in the parenchyma of the spinal cord, and the infiltration of inflammatory cells was reduced in the anti-proBDNF antibody treatment group, and only a small amount of inflammatory cells were infiltrated (FIG. 13). LFB staining showed that the myelin sheath in the spinal white matter was significantly absent in mice of the model group, and the myelin-deficient region in the spinal white matter was reduced in mice of the anti-proBDNF antibody treatment group (FIG. 14).

Figure 15:
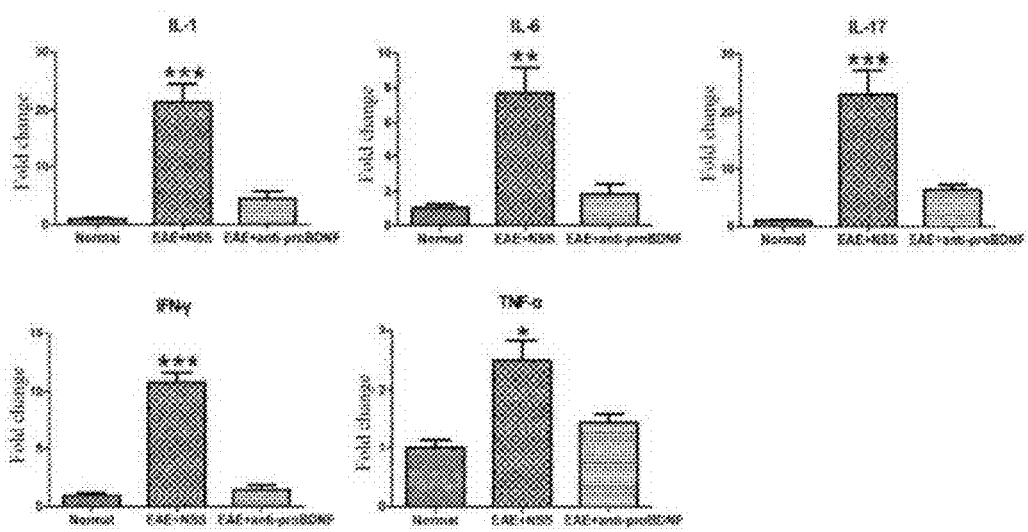
FIG. 15 shows the mRNA expression of individual inflammatory cytokines within spinal cords of EAE model mice treated with NSS and an anti-proBDNF antibody respectively at the early stage of experimental autoimmune encephalomyelitis; $*p<0.05$, $p<0.01$, $*p<0.001$, vs. the Normal group and the EAE+NSS group.

(3) Expression of inflammatory cytokines in the spinal cord: the results of Real-Time PCR are shown in FIG. 15. It is indicated that the expression of the inflammatory cytokines IL-1, IL-6, IL-17, IFN-γ and TNF-α was increased greatly, while the expression of IL-1, IL-6, IL-17, IFN-γ and TNF-α were significantly decreased in the anti-proBDNF antibody treatment group.

The results showed that the administration of the anti-proBDNF polyclonal antibody at the early stage of the disease could significantly improve the neurological function score of the model mice, and inhibit the inflammatory cell infiltration of the spinal cord and demyelination and the release of the inflammatory mediators in the model mice.

Example 12

Use of Anti-proBDNF Polyclonal Antibody in the Peak Stage of EAE

1. Experimental Animals 6- to 8-week-old female SPF-grade C57BL/6 mice, weighed 18-20 g (provided by the Department of Laboratory Animals, Central South University), were used in this experiment. Feeding conditions were as follows: clean grade, 5-6 mice/cage, water and feed ad libitum; the mice with a paralysis level of 3 or more and the dying mice were housed in a single cage during the experiment, and the mouse food was given after being macerated in feeding water. The experimental animals were completely randomized.

2. Preparation of EAE Model

The mice were anesthetized with sevoflurane. The completely emulsified MOG35-55 (3 mg/ml)/CFA (H37RA, 4 mg/ml) was subcutaneously injected into the left and right sides of the upper back and the left root of the tail of the mice at a dose of 150 μl/mouse. In addition, the mice were intraperitoneally injected with pertussis toxin PTX (0.5 μg/100 μl) at a dose of 50 μl/mouse, and were injected again with the same dose of PTX after 48 hours. On day 7, MOG35-55 (3 mg/ml)/CFA (H37RA, 2 mg/ml) was subcutaneously injected into the left and right sides of the lower back and the right root of the tail of the immunized mice at a dose of 150 μl/mouse.

3. Grouping of Animals and Administration 30 mice were randomized into three groups, 10 mice per group:

(1) normal group (Normal);

(2) model group (EAE+NSS): 17 days after modeling, an equal volume of normal sheep serum was intraperitoneally injected at a dose of 0.2 ml/mouse each day for 7 consecutive days;

(3) model+anti-proBDNF antibody treatment group (EAE+anti-proBDNF): 17 days after modeling, when the EAE model mice were at the peak stage of the disease, the mice began to receive treatment with intraperitoneally injected anti-proBDNF polyclonal antibody once a day for 7 consecutive days (2.5 mg/kg, 0.2 ml/mouse/day).

4. Experimental Post-Processing (1) Clinical scoring of the EAE model: after modeling, clinical scoring was performed every day. The scoring criteria are as follows: 0, no clinical symptoms; 0.5, weakness of tail; 1, paralysis of tail; 2, loss of coordination movement disappears; 2.5, paralysis of a unilateral hind limb; 3, paralysis of bilateral hind limbs; 3.5, paralysis of bilateral hind limbs with weakness of a forelimb; 4, paralysis of a forelimb; 5, dying or death. The score was recorded as 5 on the day when the mouse was found to be dead, and the score was no longer recorded from the next day.

(2) HE staining & sectioning and pathological scoring:

The mice of 35 days after modeling (5 mice per group) were sacrificed through perfusion. The spinal cord was removed, and dehydrated, hyalinized, subjected to waxdip, made into a wax block, and sectioned (4 μm) for HE staining according to the conventional method. Infiltration of inflammatory cells was observed.

(3) LFB staining: the sections were stained according to the conventional LFB staining method, and the demyelination was observed.

(4) Detection of spinal cord disease-related gene expression:

The spinal cords of the mice of 35 days after modeling (5 mice in each group) were detected by real-time PCR for the expression levels of proinflammatory cytokines IL-1, IL-6, IL-17, IFN-γ and TNF-α.

5. Analysis of Data Graphpad prism software 5.0 was used for analysis. It is considered as significant difference if p<0.05.

Figure 16:
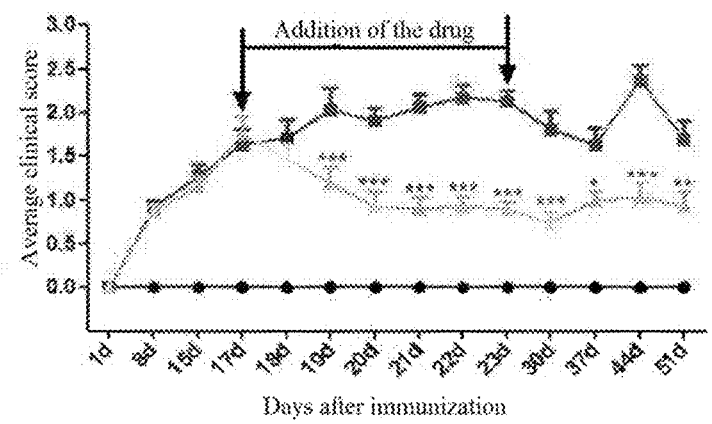
FIG. 16 shows the comparison of clinical scores of EAE model mice treated with NSS and an anti-proBDNF antibody respectively at the peak stage of experimental autoimmune encephalomyelitis; $p<0.01$, $*P<0.001$, vs. the EAE+NSS group.

6. Results (1) Onset of the disease in the model mice: the neurologic impairment of the EAE model mice treated with the anti-proBDNF polyclonal antibody was significantly reduced, and the clinical score after the treatment was basically stable at about 1 (FIG. 16).

Figure 17:
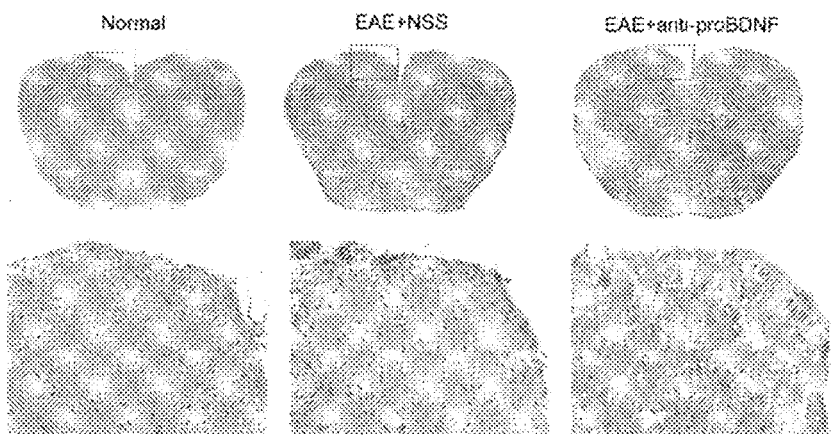
FIG. 17 shows the HE staining of spinal cords of EAE model mice treated with NSS and an anti-proBDNF antibody respectively at the peak stage of experimental autoimmune encephalomyelitis.
Figure 18:
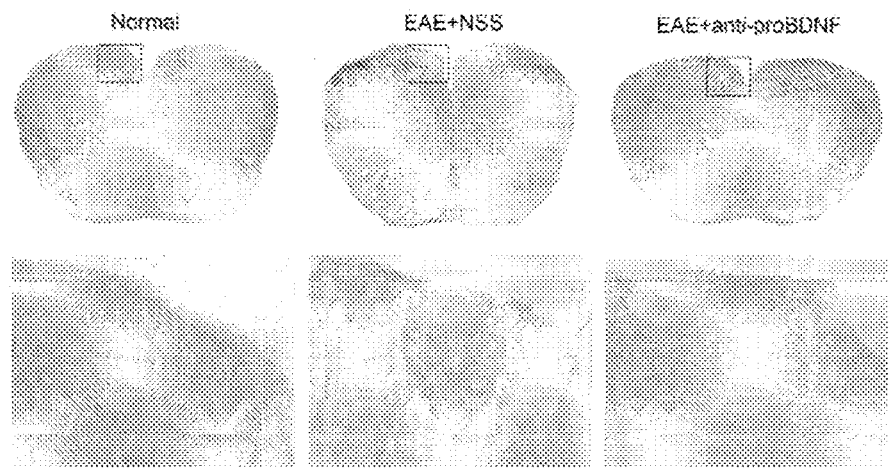
FIG. 18 shows the LFB staining of spinal cords of EAE model mice treated with NSS and an anti-proBDNF antibody respectively at the peak stage of experimental autoimmune encephalomyelitis.

(2) Pathological section and pathological damage score: the results of light microscopy showed that the inflammatory cells in mice of the model group were densely distributed in the parenchyma of the spinal cord, and the infiltration of inflammatory cells was reduced in the anti-proBDNF antibody treatment group, and only a small amount of inflammatory cells were infiltrated (FIG. 17). LFB staining showed that the myelin sheath in the spinal white matter was significantly absent in mice of the model group, and the myelin-deficient region in the spinal white matter was reduced in mice of the proBDNF antibody treatment group (FIG. 18).

Figure 19:
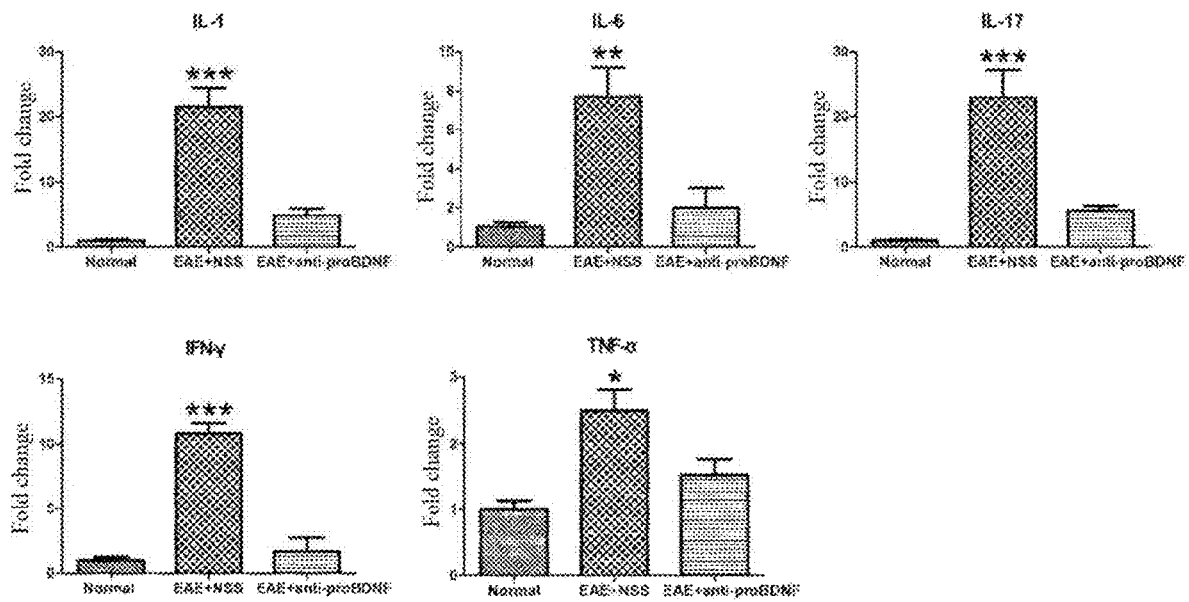
FIG. 19 shows the mRNA expression of individual inflammatory cytokines within spinal cords of EAE model mice treated with NSS and an anti-proBDNF antibody respectively at the peak stage of experimental autoimmune encephalomyelitis; $*p<0.05$, $p<0.01$, $*p<0.001$, vs. the Normal group and the EAE+NSS group.

(3) Expression of inflammatory cytokines in the spinal cord: the results of Real-Time PCR are shown in FIG. 19. It is indicated that the expression of the inflammatory cytokines IL-1, IL-6, IL-17, IFN-γ and TNF-α was increased greatly, while the expression of IL-1, IL-6, IL-17, IFN-γ and TNF-α were significantly decreased in the anti-proBDNF antibody treatment group.

The results showed that the administration of the anti-proBDNF antibody at the peak stage of the disease could significantly improve the neurological function score of the model mice, and inhibit the inflammatory cell infiltration of the spinal cord and demyelination and the release of the inflammatory mediators in the model mice.

Example 13

Figure 20:
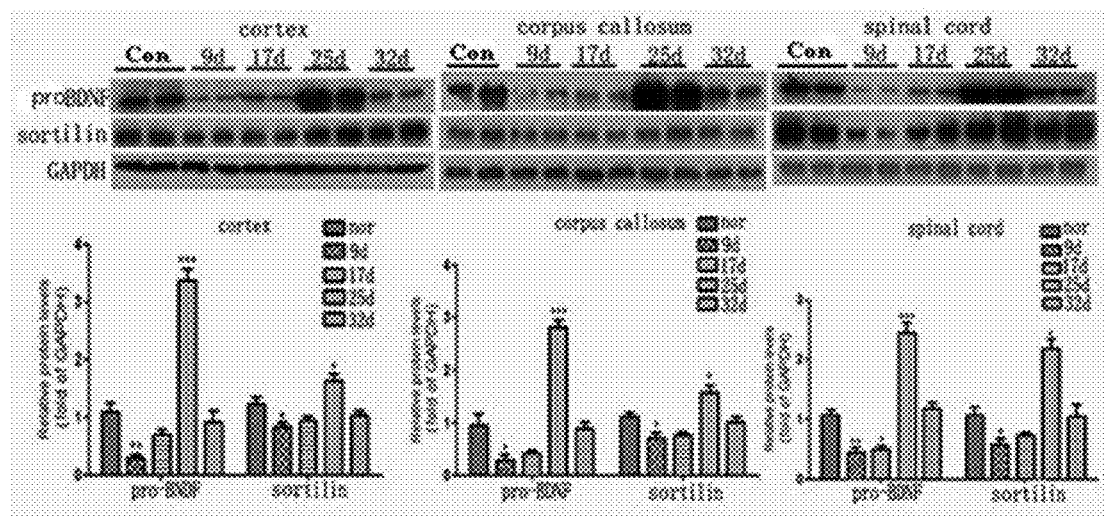
FIG. 20 shows proBDNF and sortilin expression in cortex, corpus callosum and spinal cord at day 9, day 17, day 25 and day 32 after EAE induction ($*p<0.05$, $p<0.01$, $*p<0.001$ versus control).
Figure 21:
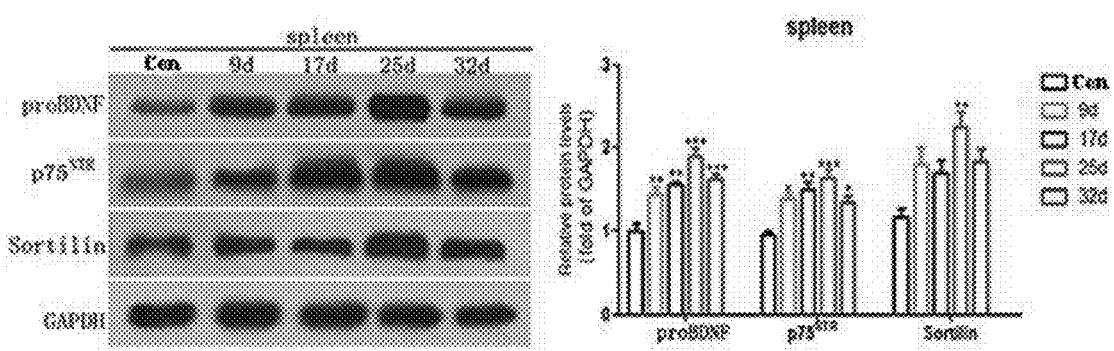
FIG. 21 shows upregulation of proBDNF in the spleen at the indicated time points after EAE induction ($*p<0.05$, $p<0.01$, $*p<0.001$ versus control).

Spatial and Temporal Expression of proBDNF and Receptor Thereof in EAE Mouse Model EAE mouse model was established according to Example 9. Animals were sacrificed at day 9, day 17, day 25, and day 32 after EAE induction. Western blot assay was conducted to determine the expression of proBDNF and its receptors, sortilin and $p75^{NTR}$. Primary antibodies used were monoclonal anti-proBDNF (2B11), p75NTR (Abcam) and sortilin (Alomone labs); and secondary antibody that were used was horseradish peroxide linked sheep anti-rabbit or sheep anti-mouse antibody (1:1000, Vector Laboratories, Burlingame, Calif.). Mouse anti-GAPDH was used as an internal control, and the relative expression of the proteins were analyzed with Image J. As shown in FIG. 20, proBDNF is only mildly expressed in cortex, corpus callosum and spinal cord. After EAE induction, expression of proBDNF and sortilin were significantly lowered at day 9 and day 17, while significantly increased at day 25 ($p<0.05$ vs. control). In spleen, the expression of both proBDNF and p75NTR were increased significantly ($p<0.05$ vs. control) (at day 9, day 17, day 25, and day 32), while the expression of sortilin was mainly increased significantly at day 25.

Figure 22:
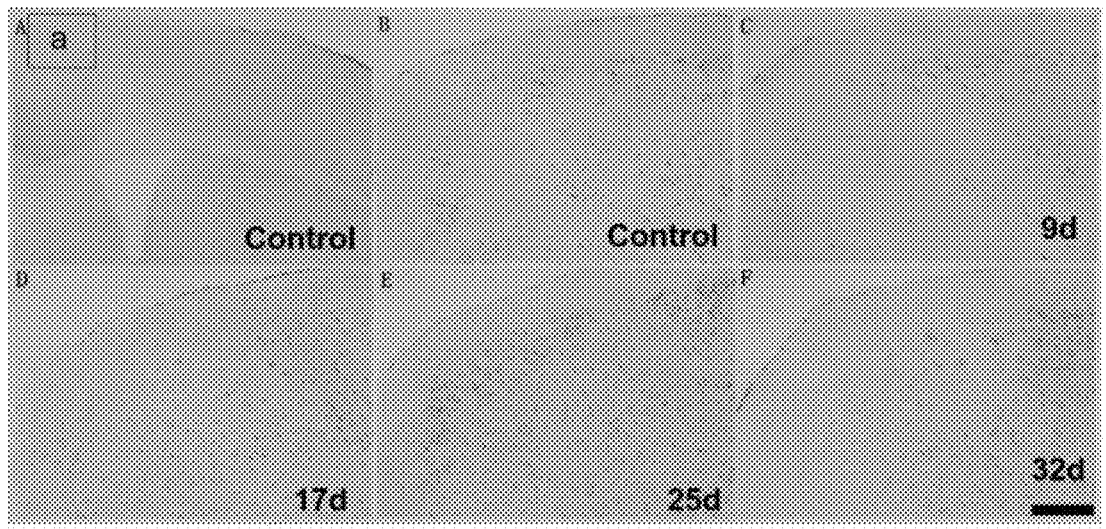
FIG. 22 shows representative proBDNF immunoreactivity in cortex at different time points after EAE induction. B is the higher magnification of the box (a) in (A). Scale bar=500 μm (A), Scale bar=100 μm (B-F).
Figure 23:
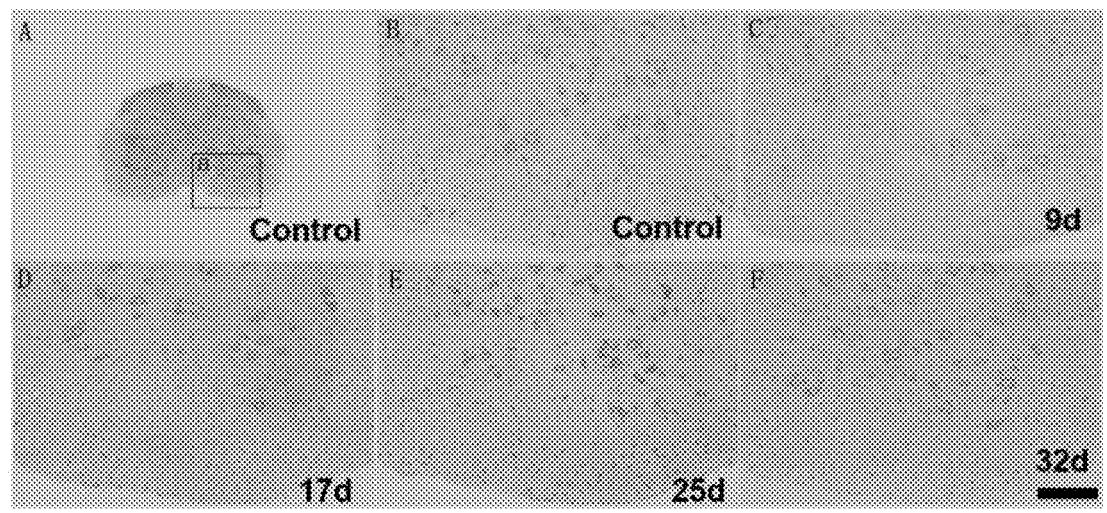
FIG. 23 shows proBDNF expression in spinal cord at different time point after EAE induction by IHC. The box (a) in (A) indicate the areas chosen for quantitative analysis. Scale bar=500 μm (A), Scale bar=100 μm (B-F).

Immunohistochemistry assay was carried out on brain tissues in order to examine proBDNF expression in EAE model of different stages. As shown in FIG. 22 and FIG. 23, upregulation of proBDNF expression was observed in both cortex and spinal cord at day 25 after EAE induction. In contrast, proBDNF expression was significantly downregulated at day 9 of EAE induction and proBDNF was mildly expressed in control.

Example 14

Expression of proBDNF and p75NTR in Immune Cells of EAE Mouse Model

EAE mouse model was established according to Example 9. Peripheral blood and spleen were collected at day 9 and day 25 after EAE induction, respectively. Mononuclear cells were isolated and Alex Fluor® 488 conjugated secondary antibodies (Rabbit anti sheep, with sheep IgG1 serving as isotype control) were used to stain the primary antibody conjugates. Results from Flow Cytometry were shown in FIG. 24, FIG. 25, FIG. 26, and FIG. 27.

Figure 24:
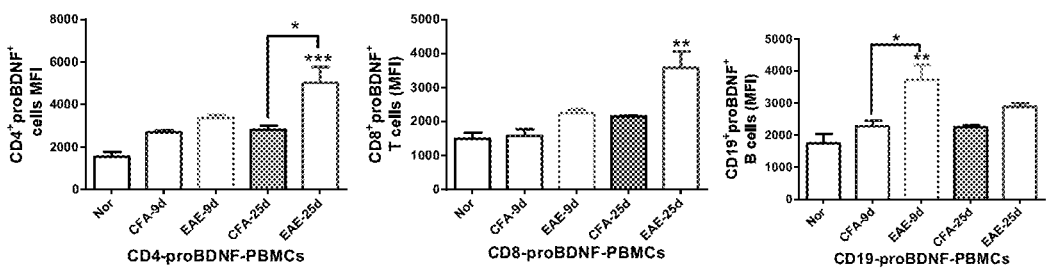
FIG. 24 shows flow cytometry analysis of proBDNF expression in peripheral blood mononuclear cells (PBMCs). Quantitative analysis of proBDNF expression in $CD4^+$ T cells, $CD8^+$ T cells and $CD19^+$ B cells. MFI: Mean fluorescence intensity. ($*p<0.05$, $p<0.01$, $*p<0.001$)
Figure 25:
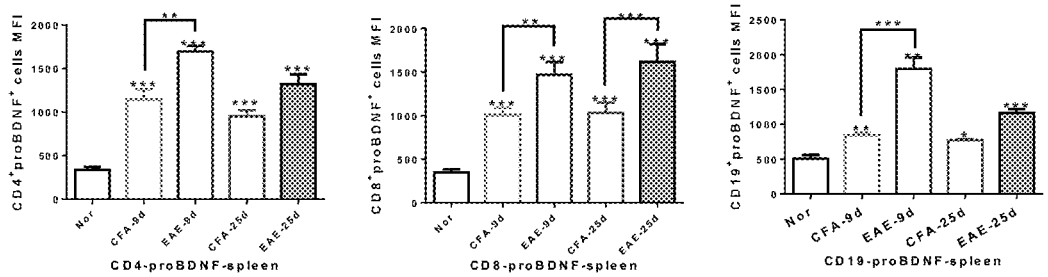
FIG. 25 shows expression of proBDNF in $CD4^+$, $CD8^+$ T cells and $CD19^+$ B cells in the spleen at day 9 or 25 after EAE induction. ($*p<0.05$, $p<0.01$, $*p<0.001$)

As shown by FIG. 24 and FIG. 25, upregulation of proBDNF expression was observed in CD19+B cells at day 9, while at day 25, upregulation of proBDNF expression was mainly observed in CD4+ and CD8+ T cells; and in spleen, upregulation of proBDNF expression was observed in CD3+, CD4+ and CD19+ cells at both day 9 and day 25. These results indicate that B and T cells are important source of proBDNF during the progress of EAE.

Figure 26:
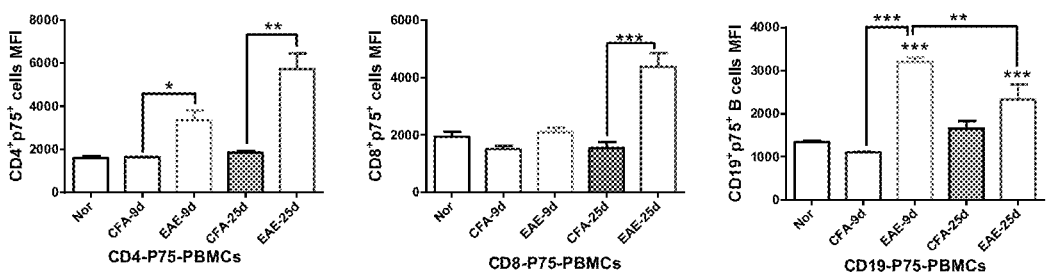
FIG. 26 shows expression of $p75^{NTR}$ in $CD4^+$, $CD8^+$ T cells and $CD19^+$ B cells in the PBMCs at day 9 or 25 after EAE induction. ($*p<0.05$, $p<0.01$, $*p<0.001$)
Figure 27:
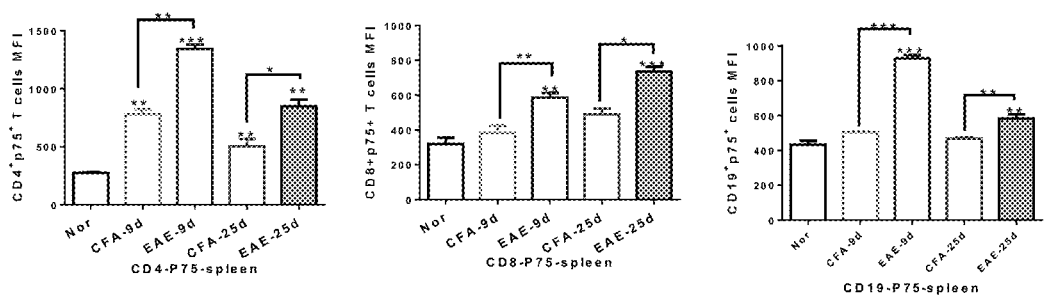
FIG. 27 shows expression of proBDNF in $CD4^+$, $CD8^+$ T cells and $CD19^+$ B cells in the spleen at day 9 or 25 after EAE induction. ($*p<0.05$, $p<0.01$, $*p<0.001$)

Results for p75NTR are shown in FIG. 26 and FIG. 27. Upregulation of p75NTR expression was observed in CD4+ and CD19+ PBMCs at day 9 and in CD4+, CD8+ and CD19+ cells at day 25. In spleen, upregulation was observed in T cells and B cells at both day 9 and day 25.

Example 15

Expression of proBDNF and p75NTR in an MS Patience

Paraffin sections were obtained from MS Research Australia Brain Bank (Australia). Routine Hematoxylin and Eosin (H&E) stain was conducted, and result was observed with optical microscope. The slide was then deparaffinized and rehydrated, epitope heat-retrived, blocked in serum, and primary antibody applied (monoclonal anti-proBDNF, Millipore, USA). Sheep anti mouse antibody was used as secondary antibody, and the slide was stained with DAB and counterstained with hematoxylin. Positive cells were observed at 100× and 400× magnification and analyzed semi-quantitatively by HMIAS-2000 imaging system.

Figure 28:
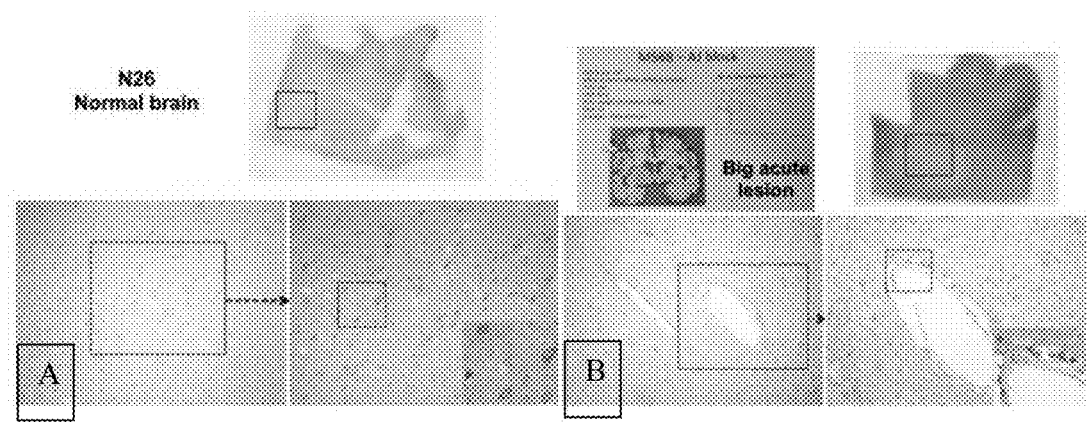
FIG. 28 shows expression of proBDNF in the normal brain and big acute regions in an MS patient. proBDNF is mildly expressed in the neurons in the normal brain (A). In the acute regions of MS patients, proBDNF is upregulated in the perivascular regions and displayed to be localized in the infiltrating inflammatory cells (B).

FIG. 28 shows the expression of proBDNF in the normal region and acute injury region of the brain of an MS patient. In the normal brain, proBDNF is mildly expressed in the neurons (A). In the acute regions of the MS patient, proBDNF expression is upregulated in the perivascular regions and displayed to be localized in the infiltrating inflammatory cells (B).

Example 16

Effect of Anti-proBDNF Polymonoclonal Antibody on Cytokine Expression in EAE Mouse Spleen and Spinal Cord Forty mice were divided into four groups: normal control group, EAE+NSS (normal sheep serum) group, EAE+D9 (early interference) group, and EAE+D17 (peak stage interference) group. EAE model was established in mice according to Example 9. On day 9, animals in the early interference group were administered with the anti-proBDNF polyclonal antibody prepared in Example 10 (i.p., 2.5 mg/kg, at 0.2 ml/animal/day, for 7 consecutive days). For animals in the peak stage disease group, polyclonal antibody was given on day 17 according to the same regimen as in the early interference group. On day 25, animals were sacrificed and spleen and spinal cord were collected. Real-Time PCR was conducted according to manufacturer's instructions, using RevertAid™ First Strand cDNA synthesis Kit (Fermentas Inc., Vilnius, Lithuania) and SsoFast™ EvaGreen® Supermix reaction cocktail (Bio-Rad Laboratories, Inc., CA, USA). Primers from GeneCopoeia, Inc. (Maryland, USA) were used and shown in the table below:

| Primer | Lot# |
| --- | --- |
| IL-6 | Mm-QRP-20563 |
| TNF-α | Mm-QPR-21418 |
| IFN-γ | Mm-QPR-20021 |
| IL-17 | Mm-QPR-21505 |
| IL-1β | Mm-QPR-21551 |
| GAPDH | Mm-QPR-20043 |

Figure 29:
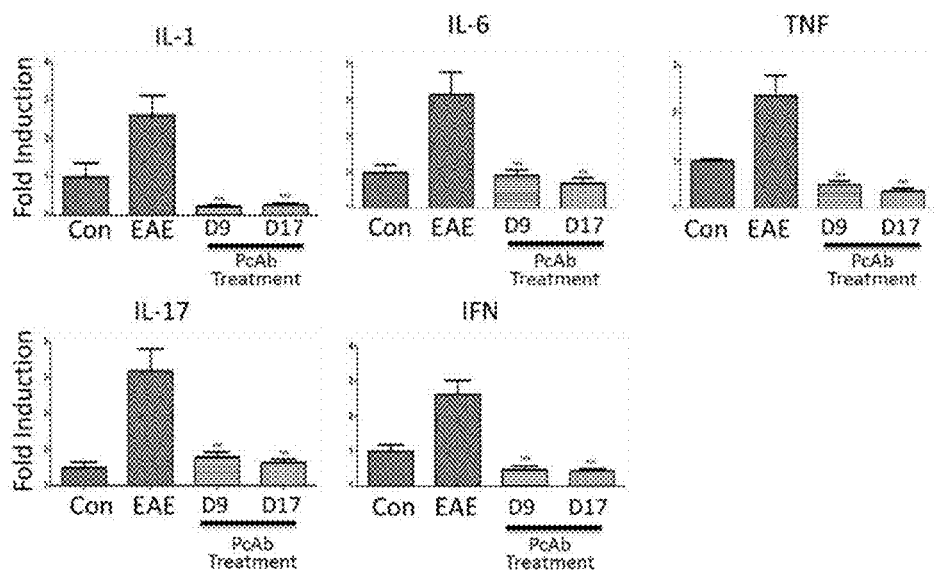
FIG. 29 shows effect of poly-Ab-proBDNF treatment on cytokines expression in the spleen in the EAE mice. In the EAE+NSS group, the cytokine expression is dramatically increased. In contrast, poly-Ab-proBDNF treatment greatly inhibits the upregulation of cytokines in the spleen.

As shown in FIG. 29, in the spleen of EAE mice, cytokines such as IL-1, IL-6, IL-17, IFN-γ and TNF-α are dramatically upregulated. For both animals of early interference group and the peak stage disease group, anti-proBDNF treatment greatly inhibits the upregulation.

Figure 30:
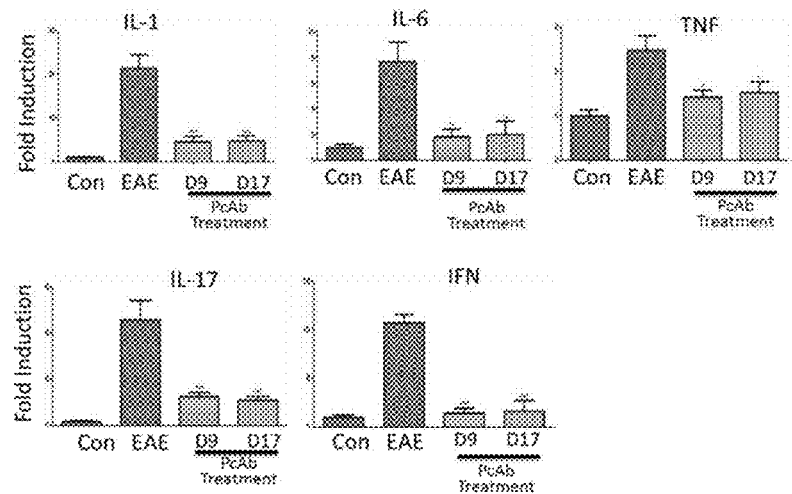
FIG. 30 shows effect of poly-Ab-proBDNF on cytokine expression in the spinal cord. Upregulation of cytokines was detected in the EAE mice. Polyclonal anti-proBDNF treatment at day 9 or day 17 inhibits the activation of cytokines.
Figure 31:
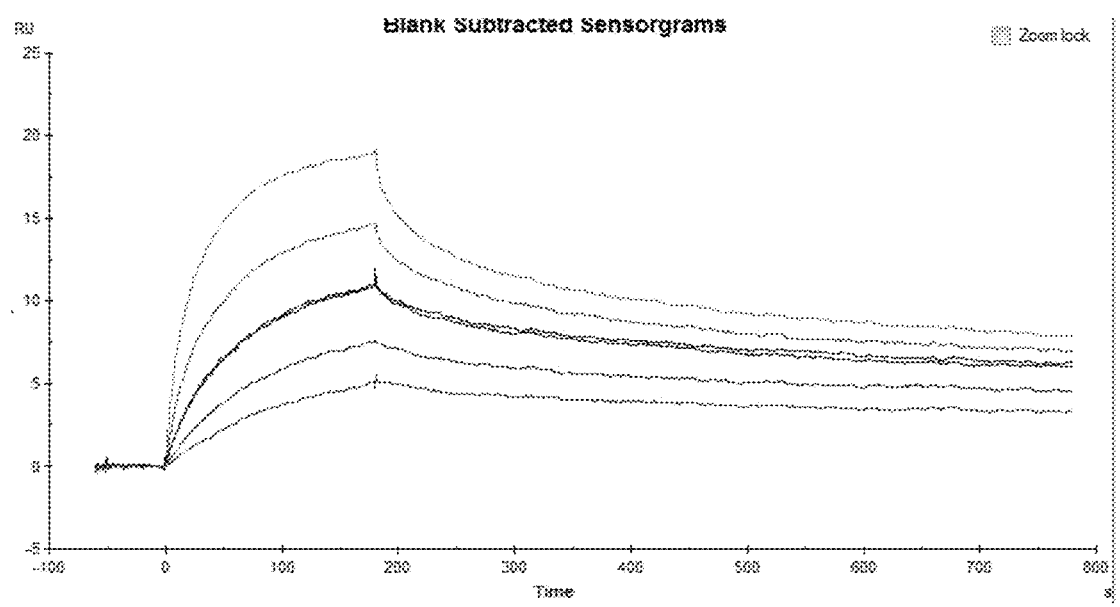
FIG. 31 shows Biacore pattern of murine monoclonal antibody 2B11.

Results for spinal cord are shown in FIG. 30. Dramatic upregulation of IL-1, IL-6, IL-17, IFN-γ and TNF-α expression was observed in EAE spinal cord. The upregulation was greatly inhibited by anti-proBDNF treatment both at early stage or peak stage.

Example 17

Binding Affinity of 2B11

Binding affinity of 2B11 against recombinant human proBDNF was measured by Surface Plasmon resonance (SPR) using Biacore T200™. 1×HBS-EP+ buffer was used as running buffer. Recombinant human proBDNF was directly coated on CM5 biosensor chip to achieve approximately 500 response units (RU). For kinetics measurements, two-fold serial dilutions (10 nM to 160 nM) were injected at 25° C. with a flow rate of 30 ul/min. Association rate ($K_a$) and dissociation rate ($K_d$) were calculated using a simple one to one Langmuir binding model (BIAcore Evaluation software version 3.2). The equilibrium dissociation constant (kD) was calculated as the ratio $K_d/K_a$. The binding affinity of 2B11 to human proBDNF is reported below:

| Antibody | Ka (1/Ms) | $K_d$ (1/s) | kD (M) |
|----------|-----------|-------------|--------|
| 2B11     | 2.876E+5  | 1.163E−3    | 4.043E−9 |

All documents mentioned in the present invention are herein incorporated by reference to the extent as if each document was individually indicated to be incorporated by reference. Furthermore, it should be understood that those skilled in the art can make various changes or modifications to the present invention after reading the above description of the present invention, and these equivalents also fall within the scope of the appended claims of the present application.

What is claimed is:

1. A method for mitigating or treating rheumatoid arthritis comprising administering to a subject in need thereof a binding molecule which specifically binds to a precursor of brain-derived neurotrophic factor, wherein the binding molecule is a monoclonal antibody comprising a heavy chain variable region having a CDR1 region with at least 95% sequence homology to SEQ ID NO: 1, a CDR2 region with at least 95% sequence homology to SEQ ID NO: 2 and a CDR3 region with at least 95% sequence homology to SEQ ID NO: 3; and a light chain variable region having a CDR1 region with at least 95% sequence homology to SEQ ID NO: 4, a CDR2 region with at least 95% sequence homology to SEQ ID NO: 5 and a CDR3 region with at least 95% sequence homology to SEQ ID NO: 6.

2. The method according to claim 1, wherein the monoclonal antibody comprises a heavy chain variable region having a CDR1 region as shown in SEQ ID NO: 1, a CDR2 region as shown in SEQ ID NO: 2 and a CDR3 region as shown in SEQ ID NO: 3; and a light chain variable region having a CDR1 region as shown in SEQ ID NO: 4, a CDR2 region as shown in SEQ ID NO: 5 and a CDR3 region as shown in SEQ ID NO: 6.

3. The method according to claim 1, wherein the heavy chain variable region of the monoclonal antibody has an amino acid sequence as shown in SEQ ID NO: 7; and the light chain variable region of the monoclonal antibody has an amino acid sequence as shown in SEQ ID NO: 8.

4. The method according to claim 3, wherein the heavy chain variable region of the monoclonal antibody is encoded by a nucleotide sequence as shown in SEQ ID NO: 11; or the light chain variable region of the monoclonal antibody is encoded by a nucleotide sequence as shown in SEQ ID NO: 12.

5. The method according to claim 1, wherein the heavy chain of the monoclonal antibody has an amino acid sequence as shown in SEQ ID NO: 9; or the light chain of the monoclonal antibody has an amino acid sequence as shown in SEQ ID NO: 10.

6. The method according to claim 5, wherein the heavy chain of the monoclonal antibody is encoded by a nucleotide sequence as shown in SEQ ID NO: 13; or the light chain of the monoclonal antibody is encoded by a nucleotide sequence as shown in SEQ ID NO: 14.

7. The method according to claim 1, wherein the binding molecule is administered to the subject at an amount in the range of 0.1-100 mg/kg body weight.

8. A method for inhibiting IL-1, IL-6, or IL-17 production, comprising administering to a subject in need thereof a binding molecule which specifically binds to a precursor of brain-derived neurotrophic factor, wherein the binding molecule is a monoclonal antibody comprising a heavy chain variable region having a CDR1 region with at least 95% sequence homology to SEQ ID NO: 1, a CDR2 region with at least 95% sequence homology to SEQ ID NO: 2 and a CDR3 region with at least 95% sequence homology to SEQ ID NO: 3; and a light chain variable region having a CDR1 region with at least 95% sequence homology to SEQ ID NO: 4, a CDR2 region with at least 95% sequence homology to SEQ ID NO: 5 and a CDR3 region with at least 95% sequence homology to SEQ ID NO: 6.

9. The method according to claim 8, wherein the monoclonal antibody comprising a heavy chain variable region having a CDR1 region as shown in SEQ ID NO: 1, a CDR2 region as shown in SEQ ID NO: 2 and a CDR3 region as shown in SEQ ID NO: 3; and a light chain variable region having a CDR1 region as shown in SEQ ID NO: 4, a CDR2 region as shown in SEQ ID NO: 5 and a CDR3 region as shown in SEQ ID NO: 6.

10. The method according to claim 8, wherein the heavy chain variable region of the monoclonal antibody has an amino acid sequence as shown in SEQ ID NO: 7; and the light chain variable region of the monoclonal antibody has an amino acid sequence as shown in SEQ ID NO: 8.

11. The method according to claim 10, wherein the heavy chain of the monoclonal antibody has an amino acid sequence as shown in SEQ ID NO: 9; or the light chain of the monoclonal antibody has an amino acid sequence as shown in SEQ ID NO: 10.

12. The method according to claim 8, wherein the binding molecule is administered to the subject at an amount in the range of 0.1-100 mg/kg body weight.

13. A method for inhibiting interferon gamma (IFN-γ) or tumor necrosis factor alpha (TNF-α) production, comprising administering to a subject in need thereof a binding molecule which specifically binds to a precursor of brain-derived neurotrophic factor, wherein the binding molecule is a monoclonal antibody comprising a heavy chain variable region having a CDR1 region with at least 95% sequence homology to SEQ ID NO: 1, a CDR2 region with at least 95% sequence homology to SEQ ID NO: 2 and a CDR3 region with at least 95% sequence homology to SEQ ID NO: 3; and a light chain variable region having a CDR1 region with at least 95% sequence homology to SEQ ID NO: 4, a CDR2 region with at least 95% sequence homology to SEQ ID NO: 5 and a CDR3 region with at least 95% sequence homology to SEQ ID NO: 6.

14. The method according to claim 13, wherein the monoclonal antibody comprising a heavy chain variable region having a CDR1 region as shown in SEQ ID NO: 1, a CDR2 region as shown in SEQ ID NO: 2 and a CDR3 region as shown in SEQ ID NO: 3; and a light chain variable region having a CDR1 region as shown in SEQ ID NO: 4, a CDR2 region as shown in SEQ ID NO: 5 and a CDR3 region as shown in SEQ ID NO: 6.

15. The method according to claim 13, wherein the heavy chain variable region of the monoclonal antibody has an amino acid sequence as shown in SEQ ID NO: 7; and the light chain variable region of the monoclonal antibody has an amino acid sequence as shown in SEQ ID NO: 8.

16. The method according to claim 13, wherein the heavy chain of the monoclonal antibody has an amino acid sequence as shown in SEQ ID NO: 9; or the light chain of the monoclonal antibody has an amino acid sequence as shown in SEQ ID NO: 10.

17. The method according to claim 13, wherein the binding molecule is administered to the subject at an amount in the range of 0.1-100 mg/kg body weight.

* * * * *

SEQUENCE LISTING

```
<160> NUMBER OF SEQ ID NOS: 37

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Thr Asp Tyr Tyr Met Ser
1               5                   10

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Ile Arg Asn Lys Ala Asn Gly Tyr Thr Thr Glu Tyr Ser Ser Ser
1               5                   10                  15

Val Lys Gly

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Met Asp Tyr
1

<210> SEQ ID NO 4
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Arg Ala Ser Gly Asn Ile His Asn Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Ala Gln Thr Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln His Phe Trp Ser Thr Pro Phe Thr
1               5

<210> SEQ ID NO 7
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Lys Val Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ser
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Ile Thr Met Asp Tyr Trp Gly Gln Gly Thr Ser Val Thr
            100                 105                 110

Val Ser Ser
        115

<210> SEQ ID NO 8
<211> LENGTH: 108
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 8

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Lys Lys Gln Gly Lys Ser Pro His Leu Leu Val
        35                  40                  45

Tyr Asn Ala Gln Thr Leu Ala Asp Gly Val Pro Ser Arg Phe Ser Gly
50                  55                  60

Ser Ala Ser Gly Thr Gln Tyr Ser Leu Lys Ile Asp Ser Leu Gln Pro
65                  70                  75                  80

Glu Asp Phe Gly Ser Tyr Tyr Cys Gln His Phe Trp Ser Thr Pro Phe
                85                  90                  95

Thr Phe Gly Ser Gly Thr Lys Leu Glu Ile Lys Arg
            100                 105
```

<210> SEQ ID NO 9
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Arg Val Leu Ile Leu Leu Trp Leu Phe Thr Ala Phe Pro Gly Phe
1               5                   10                  15

Leu Ser Glu Val Lys Val Val Glu Ser Gly Gly Gly Leu Val Gln Pro
            20                  25                  30

Gly Gly Ser Leu Arg Leu Ser Cys Ala Thr Ser Gly Phe Thr Phe Thr
        35                  40                  45

Asp Tyr Tyr Met Ser Trp Val Arg Gln Pro Pro Gly Lys Ala Leu Glu
50                  55                  60

Trp Leu Gly Phe Ile Arg Asn Lys Ala Asn Gly Tyr Thr Thr Glu Tyr
65                  70                  75                  80

Ser Ser Ser Val Lys Gly Arg Phe Thr Ile Ser Arg Asp Asn Ser Gln
                85                  90                  95

Ser Ile Leu Tyr Leu Gln Met Asn Thr Leu Arg Ala Glu Asp Ser Ala
            100                 105                 110

Thr Tyr Tyr Cys Ala Ile Thr Met Asp Tyr Trp Gly Gln Gly Thr Ser
        115                 120                 125

Val Thr Val Ser Ser Ala Ser Thr Lys Gly Pro Ser Val Phe Pro Leu
130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
210                 215                 220
```

```
Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
            245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
            290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
            325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
            355                 360                 365

Pro Ser Arg Asp Glu Leu Thr Lys Asn Gln Val Ser Leu Thr Cys Leu
            370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
    450                 455                 460

<210> SEQ ID NO 10
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asp Met Met Val Leu Ala Gln Phe Leu Ala Phe Leu Leu Leu Trp
1               5                   10                  15

Phe Pro Gly Ala Arg Cys Asp Ile Gln Met Thr Gln Ser Pro Ala Ser
            20                  25                  30

Leu Ser Ala Ser Val Gly Glu Thr Val Thr Ile Thr Cys Arg Ala Ser
            35                  40                  45

Gly Asn Ile His Asn Tyr Leu Ala Trp Tyr Gln Lys Lys Gln Gly Lys
            50                  55                  60

Ser Pro His Leu Leu Val Tyr Asn Ala Gln Thr Leu Ala Asp Gly Val
65                  70                  75                  80

Pro Ser Arg Phe Ser Gly Ser Ala Ser Gly Thr Gln Tyr Ser Leu Lys
            85                  90                  95

Ile Asp Ser Leu Gln Pro Glu Asp Phe Gly Ser Tyr Tyr Cys Gln His
            100                 105                 110
```

```
Phe Trp Ser Thr Pro Phe Thr Phe Gly Ser Gly Thr Lys Leu Glu Ile
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 11
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gaggtgaagg tggtggagtc tgaggaggc ttggtacagc ctgggggctc tctgagactc      60
tcctgtgcaa cttctgggtt caccttcact gattactaca tgagttgggt ccgccagcct    120
ccaggaaagg cacttgagtg gttgggtttt attagaaaca agctaatgg ttacacaaca     180 gagtacagtt catctgtgaa gggtcgattc accatctcca gagataattc ccaaagcatc    240
ctctatcttc aaatgaacac cctgagagct gaggacagtg ccacttatta ctgtgcaatc    300
actatggact actggggtca aggaacctca gtcaccgtct cctca                    345
```

<210> SEQ ID NO 12
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
gacatccaga tgactcagtc tccagcctcc ctatctgcat ctgtgggaga aactgtcacc     60
atcacatgtc gagcaagtgg gaatattcac aattatttag catggtatca agagaaacag   120
ggaaaatctc ctcacctcct ggtctataat gcacaaacct tagcagatgg tgtgccatca    180
aggttcagtg gcagtgcatc aggaacacaa tattctctca agatcgacag cctgcagcct    240
gaagattttg ggagttacta ctgtcaacat ttttggagta ctccattcac gttcggctcg    300
gggacaaagt tggaaataaa acgt                                           324
```

<210> SEQ ID NO 13
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atgagagtgc tgattctttt gtggctgttc acagcctttc ctggtttcct gtctgaggtg      60
aaggtggtgg agtctggagg aggcttggta cagcctgggg gctctctgag actctcctgt     120
gcaacttctg ggttcacctt cactgattac tacatgagtt gggtccgcca gcctccagga     180
aaggcacttg agtggttggg ttttattaga aacaaagcta atggttacac aacagagtac     240
agttcatctg tgaagggtcg attcaccatc tccagagata attcccaaag catcctctat     300
cttcaaatga cacgctgag agctgaggac agtgccactt attactgtgc aatcactatg     360
gactactggg gtcaaggaac ctcagtcacc gtctcctcag cctccaccaa gggcccatcg     420
gtcttccccc tggcaccctc ctccaagagc acctctgggg gcacagcggc cctgggctgc     480
ctggtcaagg actacttccc cgaaccggtg acggtgtcgt ggaactcagg cgccctgacc     540
agcggcgtgc acaccttccc ggctgtccta cagtcctcag gactctactc cctcagcagc     600
gtggtgaccg tgccctccag cagcttgggc acccagacct acatctgcaa cgtgaatcac     660
aagcccagca acaccaaggt ggacaagaaa gttgagccca aatcttgtga caaaactcac     720
acatgcccac cgtgcccagc acctgaactc ctggggggac cgtcagtctt cctcttcccc     780
ccaaaaccca aggacaccct catgatctcc cggacccctg aggtcacatg cgtggtggtg     840
gacgtgagcc acgaagaccc tgaggtcaag ttcaactggt acgtggacgg cgtggaggtg     900
cataatgcca agacaaagcc gcgggaggag cagtacaaca gcacgtaccg tgtggtcagc     960
gtcctcaccg tcctgcacca ggactggctg aatggcaagg agtacaagtg caaggtctcc    1020
aacaaagccc tcccagcccc catcgagaaa accatctcca aagccaaagg cagccccga    1080
gaaccacagg tgtacaccct gcccccatcc cgggatgagc tgaccaagaa ccaggtcagc    1140
ctgacctgcc tggtcaaagg cttctatccc agcgacatcg ccgtggagtg ggagagcaat    1200
gggcagccgg agaacaacta caagaccacg cctcccgtgc tggactccga cggctccttc    1260
ttcctctata gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaa                                                             1389
```

<210> SEQ ID NO 14
<211> LENGTH: 708
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atggacatga tggtccttgc tcagtttctt gcattcttgt tgctttggtt tccaggtgca      60
agatgtgaca tccagatgac tcagtctcca gcctccctat ctgcatctgt gggagaaact     120
gtcaccatca catgtcgagc aagtgggaat attcacaatt atttagcatg gtatcagaag     180
aaacagggaa aatctcctca cctcctggtc tataatgcac aaaccttagc agatggtgtg     240
ccatcaaggt tcagtggcag tgcatcagga acacaatatt ctctcaagat cgacagcctg     300
cagcctgaag attttgggag ttactactgt caacattttt ggagtactcc attcacgttc     360
ggctcgggga caaagttgga aataaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
```

```
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt                 708
```

```
<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcgaattccc catgaaagaa gcaaacatcc                                     30
```

```
<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccgctcgagt tatcttcccc ttttaatggt caatg                               35
```

```
<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gctggctagc acccatgaaa gaagcaaaca tccgag                              36
```

```
<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccgctcgagg tggcgccgga ccctcatg                                       28
```

```
<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctggctagc gcgcccatga aagaagcaaa c                                   31
```

```
<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 20
ccgctcgagg cgccgaaccc tcatagacat g                          31

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catggctaca tgctgacagc cta                                   23

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccagagttcc aggtcactgt cact                                  24

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aggtgctgtc tttgctgtcc tg                                    22

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgcggatcca cagcctactg atgatcagtc gatg                       34

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccagggtcac catggagtta gttt                                  24

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gttcaagaag cacacgactg agg					23

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggctgttcac agcctttcct ggtttcctgt ctgaggtgaa ggtggtggag					50

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgatgggccc ttggtggagg ctgaggagac ggtgactg					38

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcctccacca agggcccatc ggtcttcccc ctgg					34

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgcttttgag agggagtact cac					23

<210> SEQ ID NO 31
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cctagctagc caccatgaga gtgctgattc ttttgtggct gttcacagcc tttcct					56

<210> SEQ ID NO 32
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cttgcattct tgttgctttg gtttccaggt gcaagatgtg acatccagat gactc        55

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agccaccgta cgttttattt ccaactttg                                    29

<210> SEQ ID NO 34
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gatcgatatc caccatggac atgatggtcc ttgctcagtt tcttgcattc ttgttg       56

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ctagcgccga accctcatag a                                            21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttagcgccga accctcatag a                                            21

<210> SEQ ID NO 37
<211> LENGTH: 110
<212> TYPE: PRT
<213> ORGANISM: Homo sapiens

<400> SEQUENCE: 37

Ala Pro Met Lys Glu Ala Asn Ile Arg Gly Gln Gly Gly Leu Ala Tyr
1               5                   10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Val
        35                  40                  45

Ile Glu Glu Leu Leu Asp Glu Asp Gln Lys Val Arg Pro Asn Glu Glu
    50                  55                  60

Asn Asn Lys Asp Ala Asp Leu Tyr Thr Ser Arg Val Met Leu Ser Ser
65                  70                  75                  80

-continued

```
Gln Val Pro Leu Glu Pro Pro Leu Leu Phe Leu Leu Glu Glu Tyr Lys
                85                  90                  95

Asn Tyr Leu Asp Ala Ala Asn Met Ser Met Arg Val Arg Arg
                100                 105                 110
```